United States Patent [19]
Paulik et al.

[11] Patent Number: 4,690,912

[45] Date of Patent: * Sep. 1, 1987

[54] RHODIUM-CONTAINING CARBONYLATION CATALYSTS WITH HALOGEN-CONTAINING PROMOTER

[75] Inventors: Frank E. Paulik, St. Louis; Arnold Hershman, Frontenac; Walter R. Knox, Town & Country, all of Mo.; James F. Roth, Allentown, Pa.

[73] Assignee: Monsanto Company, St. Louis, Mo.

[ * ] Notice: The portion of the term of this patent subsequent to May 18, 1988 has been disclaimed.

[21] Appl. No.: 541,845

[22] Filed: Oct. 14, 1983

Related U.S. Application Data

[63] Continuation-in-part of Ser. No. 248,777, Mar. 30, 1981, abandoned, which is a continuation-in-part of Ser. No. 824,577, Aug. 15, 1977, abandoned, which is a continuation of Ser. No. 391,103, Aug. 27, 1973, abandoned, which is a continuation-in-part of Ser. No. 263,332, Jun. 15, 1972, Pat. No. 3,813,428, Ser. No. 128,519, Mar. 26, 1971, Pat. No. 3,769,326, and Ser. No. 2,413, Mar. 12, 1970, Pat. No. 3,769,329, which is a continuation-in-part of Ser. No. 701,637, Jan. 30, 1968, abandoned, which is a continuation-in-part of Ser. No. 628,581, Apr. 5, 1967, abandoned, said Ser. No. 263,332, is a continuation of Ser. No. 752,794, Aug. 15, 1968, abandoned, which is a continuation-in-part of Ser. No. 628,581, , said Ser. No. 128,519, is a continuation of Ser. No. 2,377, Jan. 12, 1970, abandoned, which is a continuation-in-part of Ser. No. 628,581.

[51] Int. Cl.$^4$ .................. B01J 31/20; B01J 31/24; B01J 31/18; B01J 27/08

[52] U.S. Cl. .................... 502/161; 502/155; 502/166; 502/169; 502/174; 502/230; 560/232; 562/519; 562/607; 562/406

[58] Field of Search .............. 502/166, 161, 155, 230, 502/169, 174

[56] References Cited

U.S. PATENT DOCUMENTS

| | | | |
|---|---|---|---|
| 2,710,878 | 6/1955 | Glasebbrook | 560/232 |
| 2,739,169 | 3/1956 | Hagemeyer, Jr. | 560/232 |
| 3,020,314 | 2/1962 | Alderson | 568/387 |
| 3,065,242 | 11/1962 | Alderson et al. | 560/233 |
| 3,260,767 | 7/1966 | Bajars | 585/619 |
| 3,338,961 | 8/1967 | Closson et al. | 560/114 |
| 3,367,961 | 2/1968 | Brewbaker | 560/130 |
| 3,459,780 | 8/1969 | Wilkinson | 502/166 |
| 3,487,112 | 12/1969 | Pavlik et al. | 568/454 |
| 3,497,488 | 2/1970 | Dawans et al. | 502/155 |
| 3,515,757 | 6/1976 | Sibert | 502/161 |
| 3,579,552 | 5/1971 | Craddock et al. | 502/406 |
| 3,697,611 | 10/1972 | Magoon | 585/642 |
| 3,855,307 | 12/1974 | Romy et al. | 502/161 |
| 3,933,861 | 1/1976 | Kvrkov | 502/230 |
| 4,046,807 | 9/1977 | Kuckertz | 502/151 |

FOREIGN PATENT DOCUMENTS 837643  3/1970  Canada .............. 502/166

OTHER PUBLICATIONS

*A Comprehensive Treatise On Inorganic and Theoretical Chemistry* (1936), J. W. Mellor—Longmans Greem & Co., N.Y.—vol. XV, pp. 581 and 582.

Primary Examiner—P. E. Konopka
Attorney, Agent, or Firm—Wendell W. Brooks; Arthur E. Hoffman

[57] ABSTRACT

A catalyst system having high activity and selectivity to carbonylation products comprises a rhodium-containing catalytically active component and a halogen-containing promoter component, the halogen being selected from the group consisting of bromine, iodine, bromide compounds, and iodide compounds.

13 Claims, No Drawings

RHODIUM-CONTAINING CARBONYLATION CATALYSTS WITH HALOGEN-CONTAINING PROMOTER

CROSS-REFERENCE TO RELATED APPLICATIONS

This is a continuation-in-part of copending application Ser. No. 248,777, filed Mar. 30, 1981, now abandoned which is a continuation-in-part of application Ser. No. 824,577, filed Aug. 15, 1977, now abandoned, which is a continuation of application Ser. No. 391,103, filed Aug. 27, 1973, now abandoned, which (1) is a continuation-in-part of application Ser. No. 2,413, filed Mar. 12, 1970, now U.S. Pat. No. 3,769,329, which is a continuation-in-part of application Ser. No. 701,637, filed Jan. 30, 1968, now abandoned, which is a continuation-in-part of application Ser. No. 628,581, filed Apr. 5, 1967, now abandoned, (2) is a continuation-in-part of application Ser. No. 263,332, filed June 15, 1972, now U.S. Pat. No. 3,813,428, which is a continuation of application Ser. No. 752,794, filed Aug. 15, 1968, now abandoned, which is a continuation-in-part of application Ser. No. 628,581, filed Apr. 5, 1967, now abandoned, and (3) is a continuation-in-part of application Ser. No. 128,519, filed Mar. 26, 1971, now U.S. Pat. No. 3,769,326, which is a continuation of application Ser. No. 2,377, filed Jan. 12, 1970, now abandoned, which is a continuation-in-part of application Ser. No. 628,581, filed Apr. 5, 1967, now abandoned.

BACKGROUND OF THE INVENTION

1. Field of the Invention

This invention relates to a catalyst composition or system. More particularly, this invention relates to a catalyst system for the production of carbonylation products by the reaction of a carbonylatable reactant and carbon monoxide which comprises (1) a rhodium-containing catalytically active component and (2) a halogen-containing promoter component, the halogen being selected from the group consisting of bromine, iodine, bromide compounds, and iodide compounds.

2. Description of the Prior Art

Carbonylation catalysts for the production of carbonylation products are known in the art, with many being based on cobalt and using a halide promoter. Examples of such catalysts are described in U.S. Pat. No. 2,789,137 and U.S. Pat. No. 2,730,546, both to Reppe et al.

The Reppe et al '137 patent discloses the production of acetic anhydride from dimethyl ether or methyl acetate by reaction of either of these compounds with carbon monoxide in an anhydrous liquid medium having dissolved therein cobalt bromide, cobalt iodide, or a mixture thereof. Reaction conditions specified include a pressure which "should be in excess of 200 atmospheres (2.026×10⁴ kPa, 2940 psi), with pressures between 400 and 800 atmospheres (4.053×10⁴–8.11×10⁴ kPa, 5880–11,760 psi) being preferred, and temperatures in the range of 100°–250° C., preferably between 150° C. and 200° C. The catalysts can also be in the form of cobalt metal itself or other cobalt compounds in combination with free bromine, or iodine or of compounds thereof such as alkyl bromides or iodides. Additional inert solvents such as the lower N-alkylpyrrolidones, in particular, N-methylpyrrolidone, acetic acid, or acetic anhydride itself are used to maintain the catalyst at least partly in the dissolved state.

The Reppe et al '546 patent is directed to the synthesis of low-molecular weight saturated aliphatic carboxylic acids, their esters and anhydrides by treating lower fatty acid esters of lower aliphatic saturated alcohols such as methyl acetate with carbon monoxide-containing gases under superatmospheric pressure at elevated temperatures in the presence of complex cobalt halides which contain in the molecule, in addition to the cobalt halide, an organic onium halide, for example, an ammonium or phosphonium halide. Reaction temperatures between 70° C. and 250° C. are preferred but higher temperatures, for example, up to 300° C. may also be used. Pressures are superatmospheric, preferably above 50 atmospheres (5.066×10³ kPa, 735 psi) and most preferably in the range from 200 to 300 atmospheres (2.026×10⁴ kPa to 4.053×10⁴ kPa, 2940 psi to 5880 psi), although there reportedly is no principal obstacle against using higher pressures such as 700 or 800 atmospheres (7.093×10⁴ or 8.11×10⁴ kPa, 10,290 or 11,760 psi).

Certain disadvantages of the catalysts described in the prior art are catalyst instability, lack of product selectivity, and low levels of catalyst activities. One particular disadvantage of such catalysts results from their reliance or dependence upon metal carbonyls or modified metal carbonyls, such as dicobalt octacarbonyl, iron carbonyl, and nickel carbonyl, all of which require the use of high partial pressures of carbon monoxide to remain stable under the necessarily high reaction temperatures employed during carbonylation reactions. Of particular importance is dicobalt octacarbonyl which requires partial pressures of carbon monoxide as high as 2.068×10⁴ kPa-G to 6.839×10⁴ kPa-G (3,000 psig to 10,000 psig) under carbonylation conditions of 175° C. to 300° C.

Still another disadvantage of the carbonylation catalyst systems of the prior art is their relatively low level of activity. This low level of activity requires high catalyst concentrations, long reaction times, and high temperatures to obtain substantial reaction rates and conversions. Consequently, very large and costly processing equipment is required.

Another disadvantage of the catalyst systems of the prior art is their inability to maintain high selectivity to the desired carbonylation product at temperatures required for high conversion levels and high reaction rates. At these higher temperatures, undesirable by-products such as carbonylation products of higher carbon number than desired, carbon dioxide, methane, and water are formed, thereby resulting in substantial yield losses and necessitating additional product purification and recycle steps in the processing.

Accordingly, research effort are continually being made to define new or improved catalyst systems and methods and processes of preparing highly active new catalyst systems having high selectivities to the desired products in particular processes. The discovery of the catalyst system of the instant invention which does provide a more reactive and more stable carbonylation catalyst system than those known to the prior art is therefore believed to be a decided advance in the catalyst art.

SUMMARY OF THE INVENTION

It is an object of this invention to provide a novel catalyst system or composition highly effective for the carbonylation of carbonylatable reactants to yield carbonylation products.

Another object of this invention is to provide a more reactive and more stable carbonylation catalyst composition than has been heretofore described in the prior art.

Yet another object of this invention is to provide a more selective and more reactive carbonylation catalyst composition for the production of carbonylation products.

Still another object of this invention is to provide a carbonylation catalyst composition which results in the production of a high yield of the desired carbonylation product with no substantial formation of undesirable by-products.

A further object of this invention is to provide an improved and more stable catalyst system, thereby enabling the use of lower catalyst concentration, lower temperature, lower pressure, and shorter contact time than has been generally possible heretofore in carbonylation reactions and facilitating carbonylation product isolation and catalyst recovery, and recycle without substantial catalyst decomposition and loss.

To achieve these and other objects which will become apparent from the accompanying description and claims, a catalyst composition or system for the production of carbonylation products by the reaction of a carbonylatable reactant and carbon monoxide is provided which comprises (a) a rhodium-containing catalytically active component and (b) a halogen-containing promoter component, the halogen being selected from the group consisting of bromine, iodine, bromide compounds, and iodide compounds.

DESCRIPTION OF THE PREFERRED EMBODIMENTS

Carbonylation Catalyst System and Its Preparation

In accordance with this invention, a novel catalyst composition or system for the production of carbonylation products by the reaction of a carbonylatable reactant and carbon monoxide is provided which comprises (a) a rhodium-containing catalytically active component and (b) a halogen-containing promoter component, the halogen being selected from the group consisting of bromine, iodine, bromide compounds, and iodide compounds.

The rhodium-containing catalytically active component of the catalyst system can be provided from any source or by any material which will produce rhodium ions under catalyst system preparation conditions and/or carbonylation conditions. Among the materials which may be employed as the source for the rhodium-containing catalytically active component of the catalyst system of the instant invention are rhodium metal, rhodium salts, rhodium oxides, rhodium carbonyl compounds, organorhodium compounds, coordination compounds of rhodium, and the like. Specific examples of materials capable of providing the rhodium-containing catalytically active component of the catalyst system of the instant invention may be taken from the following non-limiting partial list of suitable compounds.

| | |
|---|---|
| $RhCl_3$ | $[(n-C_4H_9)_4N][Rh(CO)_2X_2]$ where $X = Cl^-, Br^-, I^-$ |
| $RhBr_3$ | $[(n-C_4H_9)_4As]_2[Rh_2(CO)_2Y_4]$ where $Y = Br^-, I^-$ |
| $RhI_3$ | $[(n-C_4H_9)_4P][Rh(CO)I_4]$ |
| $RhCl_3 \cdot 3H_2O$ | $Rh[(C_6H_5)_3P]_2(CO)Br$ |
| $RhBr_3 \cdot 3H_2O$ | $Rh[n-C_4H_9)_3P]_2(CO)Br$ |
| $Rh_2(CO)_4Cl_2$ | $Rh[(n-C_4H_9)_3P]_2(CO)I$ |
| $Rh_2(CO)_4Br_2$ | $RhBr[(C_6H_5)_3P]_3$ |
| $Rh_2(CO)_4I_2$ | $RhI[(C_6H_5)_3P]_3$ |
| $[Rh(CO)I_4]Na$ | $[Rh(CO)Br_4]Na$ |
| $Rh_2(CO)_8$ | $RhCl[(C_6H_5)_3P]_3$ |
| $Rh[(C_6H_5)_3P]_2(CO)I$ | $RhCl[(C_6H_5)_3P]H_2$ |
| $Rh[(C_6H_5)_3P]_2(CO)Cl$ | $[(C_6H_5)_3P]_3Rh(CO)H$ |
| Rh metal | $Rh_2O_3$ |
| $Rh(NO_3)_3$ | $Li[Rh(CO)_2I_2]$ |
| $RhCl[(C_6H_5)_3P]_2(CH_3I)_2$ | $[Rh(C_2H_4)_2Cl]_2$ |
| $Rh(SnCl_3)[(C_6H_5)_3P]_3$ | $K_4Rh_2Cl_2(SnCl_3)_4$ |
| $RhCl(CO)[(C_6H_5)_3As]_2$ | $K_4Rh_2Br_2(SnBr_3)_4$ |
| $RhI(CO)[(C_6H_5)_3Sb]_2$ | $K_4Rh_2I_2(SnI_3)_4$ |
| $Na[Rh(CO)_2I_2]$ | $[Rh(CO)_2I_2]K$ |
| $[Rh(CO)_2I]_2$ | |

The rhodium-containing catalytically active component of the catalyst system of the instant invention may exist as a coordination compound of rhodium, carbon monoxide, and halide such as chloride, bromide or iodide, including both neutral and ionic complexes, as well as other suitable monodentate ligands, if desired, such as amine, organophosphine, organoarsine, and/or organostibine ligands, other ligands for example, hydride, alkyl, aryl, and aryl (1–20 carbon atoms) moieties; and trihalostannate or other neutral, cationic, or anionic monodentate moiety necessary to satisfy the coordination number of the central metal atom, rhodium, and thus form a coordination compound or complex of rhodium such as $Rh_2(CO)_4Cl_2$, $Rh[(C_6H_5)_3P]_2(CO)Br$, or $RhI[(C_6H_5)_3P]_3$.

Preferred materials to provide the rhodium-containing component of the catalyst system of the instant invention are typically coordination complexes of rhodium and monodentate ligands, carbon monoxide and iodide, such as $[Rh(CO)_2I_2]^-$, $[Rh(CO)I_4]^-$, or $[Rh(CO)_2I]_2$.

The terms "coordination compound" and "coordination complex" are used herein to mean a compound or complex formed by combination of one or more electronically rich molecules or atoms capable of independent existence with one or more electronically poor molecules or atoms, each of which may also be capable of independent existence.

While not desiring to be bound by the theory of the instant invention or to limit the invention in any way, it is believed that the active catalyst component is the $[Rh(CO)_2X_2]^-$ ion. It will be noted, however, that catalysis is basically an inexact science, that is, an empirical art, unenlightened by rules decreeing certainty and predictability. It follows therefore that various other rhodium-containing species, in addition to the dihalodicarbonylrhodate (I) ion, may also be present and/or produced under catalyst system preparation conditions and/or carbonylation conditions. Such other species, if present, may in fact be, in whole or in part, the actual active catalyst component or components. In any event, whatever the actual rhodium-containing species serving as the active catalyst component, all such species are conveniently referred to as the "rhodium-containing catalytically active component". And, as previously noted, the catalyst system of the instant invention comprises a rhodium-containing catalytically active component and a halogen-containing promoter component, the halogen being selected from the group consisting of bromine, iodine, bromide compounds, and iodide compounds.

Of the materials listed as a suitable source for the rhodium-containing catalytically active component, those which do not contain a suitable halogen component (as discussed below) will necessarily require the provision of a separate source of halogen. For example, if the rhodium-containing catalytically active component source material employed is rhodium metal or $Rh_2O_3$, it will be necessary also to employ a halogen-containing material such as methyl iodide, hydrogen iodide, iodine, and the like.

The halogen-containing promoter component of the catalyst system can be provided by any source or material which will provide a halogen selected from the group consisting of bromine, iodine, bromide compounds, and iodide compounds. Halogen or halogen-containing materials suitable for use as the source of the halogen-containing promoter component may be selected from the following non-limiting list of halogen materials:

| | | | |
|---|---|---|---|
| RY | where R = | any alkyl or aryl group | e.g., $CH_3I$, $C_6H_5Br$, $CH_3CH_2I$, etc. |
| | where Y = | Br or I | |
| $Y_2$ or $Y_3^-$ | where Y = | Br or I | e.g., $Br_2$, $I_2$, $I_3^-$, etc. |
| HY | where Y = | Br or I | e.g., HBr, HI |
| RCY ‖ O | where R = and Y = | any alkyl or aryl group Br or I | e.g., $CH_3\underset{\underset{O}{\|}}{C}Cl$, etc. |
| $R_4MY$, $R_4MY_3$, or $R_3MY_2$ | where R = | any alkyl or aryl group | e.g., $(C_4H_9)_4NI$, |
| | M = N, P, As, or Sb | $(C_6H_5)_3PI_2$ and/or combinations of R, M, and Y | |
| | Y = Br or I | | |

Other non-limiting examples of such compounds of bromine and iodine include ethyl iodide, ethyl bromide, benzyl iodide, benzyl bromide, sodium iodide, sodium bromide, potassium iodide, potassium bromide, lithium iodide, lithium bromide, barium iodide, magnesium iodide, calcium iodide, 1-decyl iodide, 1-decyl bromide, and the like.

Of these materials, iodine and iodine-containing compounds (iodide compounds) are preferred for use as the halogen-containing promoter component of the catalyst system of the instant invention, with hydrogen iodide or an alkyl iodide (for example, methyl iodide) constituting the more preferred species.

The halogen-containing component of the catalyst system of the instant invention may be provided separately from the rhodium-containing catalytically active component or it may be in combined form with the rhodium-containing catalytically active component as an integral part thereof, for example, $RhI_3$, $RhI[(C_6H_5)_3P]_3$, $Rh(CO)_4Br_2$, $[Rh(CO)_2I]_2$, and the like. Generally, however, it is preferred that the halogen-containing promoter component, which may be the same as or different from any halogen or halide moiety already present in the rhodium-containing catalytically active component of the catalyst system, is separately charged to the reactor to provide an excess of halogen in the catalyst system as a promoting component over that present as ligands in the rhodium-containing catalytically active component. By excess is meant an amount of halogen to provide at least 2 atoms of halogen per atom of rhodium in the catalyst system. Ratios of halogen to rhodium expressed as atoms of halogen to atoms of rhodium are in the range from 2/1 to 50,000/1 and higher. A preferred ratio of halogen atoms to rhodium atoms is 3/1 to 5,000/1, with a ratio of 10/1 to 2,500/1 being most preferred.

The preparation of the catalyst system of the instant invention which, as previously noted, comprises (a) a rhodium-containing catalytically active component and (b) a halogen-containing promoter component, the halogen being selected from the group consisting of bromine, iodine, bromide compounds, and iodide compounds, may be accomplished by a variety of methods. As previously noted, however, it is believed that a substantial part of the rhodium-containing material employed to provide the rhodium-containing catalytically active component is converted to the monovalent state during the preparative treatment. In general, it is preferred to preform the catalyst system of the instant invention. For example, to prepare the catalyst system, the rhodium-containing component, for example, finely divided rhodium metal (powder), a simple rhodium salt or rhodium compound is dissolved in a suitable medium, and carbon monoxide is bubbled through the resultant rhodium solution, preferably while maintaining gentle heating and stirring of the rhodium solution. Thereafter, a solution of the desired halogen-containing promoter component is added to form an active catalytic solution containing the catalyst system comprising the necessary rhodium-containing catalytically active component and the halogen-containing promoter component.

Generally, the catalyst system of the instant invention may be preformed prior to charging to a carbonylation reactor, or it may be formed in situ in the carbonylation reactor. For example, to prepare the catalyst system, the rhodium-containing catalytically active component, for example, a rhodium salt such as $RhCl_3.3H_2O$ is dissolved in a suitable solvent such as a liquid carbonylatable reactant, for example, methyl acetate, and/or a carbonylation product, for example, acetic anhydride. Subsequently, carbon monoxide is bubbled through the solution where, as previously noted, it is believed that an intermediate, such as the dimer $[Rh(CO)_2Cl]_2$, is produced wherein the rhodium is in the monovalent state. The halogen-containing promoter component is then added to the above solution, for example, hydrogen iodide, elemental iodine, an alkyl iodide (with alkyl groups having 1 to 30 carbon atoms) or other halogen-containing material selected from the group consisting of bromine, iodine, bromide compounds, and iodide compounds.

Alternatively, the rhodium-containing material, for example, $RhCl_3.3H_2O$ or $Rh_2O_3.5H_2O$ may be dissolved in a suitable solvent such as acetic acid. The solution of the rhodium-containing material is then heated, for example, to 60° C.–80° C., or in general, at a temperature below the boiling point of the solvent, with stirring. Carbon monoxide is then bubbled through the resultant solution to obtain the rhodium-containing catalytically active component which, as previously noted, exists, at least in part, in the monovalent state. Subsequently, the halogen-containing promoter component, preferably iodine or an iodide compound, is added, although the halogen-containing promoter component also may be added initially.

Another embodiment of the instant invention employs compounds wherein the rhodium already exists in the monovalent state, thereby eliminating the necessity to induce a change in the rhodium valence state. For example, monovalent rhodium compounds such as Rh[(C₆H₅)₃P]₃Cl, [Rh(C₆H₅)₃P]₂(CO)Cl, and [Rh(CO)₂Cl]₂ are dissolved in a suitable solvent and carbon monoxide is subsequently passed through the solution that preferably has been warmed and stirred. Subsequent addition of the halogen-containing promoter component results in the formation of the catalyst system of the instant invention.

As a further alternative, the catalyst system of the instant invention may be prepared as a solid (for use in vapor phase carbonylation reactions). In such instances, the catalyst system from the solutions prepared as previously described is dispersed upon an inert support material which is stable under the reaction conditions to be encountered in the use of the solid supported catalyst system, such as, for example, alumdum, activated carbon, clays, alumina, silica, silica-alumina, and ceramics by known procedures for preparing supported catalysts. The proportions in which the components of the solid supported catalyst system are present can vary widely but it is usually preferred that the support material provide from about 20% up to about 99.5% by weight of the total combined weight of the catalyst system and the support. The procedures generally employed for preparing such supported catalysts involves impregnating the support with a solution of the catalyst system, separating the saturated solid, and heating to remove any residual solvents. In general, however, it is preferred to use a catalyst system solution.

If desired, the solution of the catalyst system may also contain a high boiling, inert solvent as an additional component of such solution. Such an inert solvent must have a boiling poing of at least 25° C. higher (at standard temperature and pressure) than the desired carbonylation product. Inert solvents within this category include paraffin hydrocarbons of from 10 to 30 carbon atoms, tertiary amines of 6 to 20 carbon atoms, amides of 4 to 20 carbon atoms, organic acids of from 3 to 20 carbon atoms, and esters of the aforesaid acids, heterocyclic aromatic compounds of 5 to 20 carbon atoms, as well as the chlorine-, bromine-, and iodine-containing derivatives of all of the above described solvents. Exemplary of such solvents are dodecane, hexadecane, propionic acid, octanoic acid, benzoic acid, quinoline, decalin, 1-methylnaphthalene, 2-methylnaphthalene, N-methylpyrrolidone, and the like.

In addition to the above-mentioned inert solvents that can be added to the catalyst system solution, certain other ligands can be added to increase catalyst activity, prevent precipitation and decomposition of the catalyst system and otherwise improve the overall efficiency of the catalyst system during use under carbonylation conditions. Materials such as tertiary amines can be added to the catalyst system solution. Non-limiting examples of such materials include triphenylphosphine, tri-n-butylphosphine, tri-n-butylamine, tri-n-butylstibine, tri-n-butylarsine, and the like.

Use of Carbonylation Catalyst System

As previously noted, the catalyst system of the instant invention is useful for the production of carbonylation products by the reaction of a carbonylatable reactant and carbon monoxide. Carbonylatable reactants suitable for use in the instant invention are those compounds capable of undergoing carbonylation under carbonylation conditions to yield carbonylation products. Such materials include those selected from the group consisting of compounds having the formula:

(a) $R^1$—OH wherein $R^1$ represents a hydrocarbyl group and a hydroxyhydrocarbyl group, each having 1 to 20 carbon atoms;

(b) $R^2$—X wherein $R^2$ represents a hydrocarbyl group and a halohydrocarbyl group, each having 1 to 20 carbon atoms and the halogen of the halohydrocarbyl group and X independently represent a halogen selected from the group consisting of chlorine, bromine, and iodine;

(c) $R^3$—O—$R^4$ wherein $R^3$ and $R^4$ each independently represent a hydrocarbyl group or an oxygenated hydrocarbyl group having 1 to 19 carbon atoms, with the proviso that the total number of carbon atoms in the compound does not exceed 20;

(d)

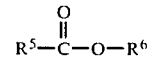

wherein $R^5$ and $R^6$ each independently represents a hydrocarbyl group having 1 to 19 carbon atoms, with the proviso that the total number of hydrocarbyl group carbon atoms in the compound does not exceed 20; and (e)

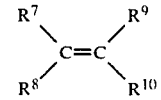

wherein $R^7$, $R^8$, $R^9$, and $R^{10}$ each independently represents hydrogen, halogen, a hydrocarbyl group, and an oxygenated hydrocarbyl group having from 1 to 20 carbon atoms, with the proviso that the total number of carbon atoms in the compound does not exceed 30.

Non-limiting examples of carbonylatable reactants defined under (a) above (alcohols) include the groups of aliphatic monohydric and polyhydric alcohols having 1 to 20 carbon atoms and aromatic alcohols having 6 to 20 carbon atoms, including methanol, ethanol, 1-propanol, 2-propanol (isopropyl alcohol), the butanols, pentanols, hexanols, phenol, cyclopentanol, cyclohexanol, 1,4-butanediol, 1,5-pentanediol, 1,6-hexanediol, catechol, resorcinol, and higher alcohols such as decanols, dodecanols, hexadecanols, nonadecanols, eicosanols, and the corresponding polyhydric alcohols, and the like.

Exemplary of the carbonylatable reactants defined under (b) above (halides) are the halides corresponding to the alcohols listed above for (a). Thus, suitable halide carbonylatable reactants include methyl chloride, methyl bromide, methyl iodide, ethyl iodide, n-propyl bromide, isopropyl iodide, 1-iodobutane (n-butyl iodide) and isomers thereof, cyclopentyl bromide, cyclohexyl iodide, phenyl chloride, phenyl bromide, phenyl iodide, 1,2-diiodobenzene, 1,4-diiodobutane, benzyl chloride, benzyl bromide, benzyl iodide, and the like.

Suitable ether and ester carbonylatable compounds are those which correspond to the ether and esters defined, respectively, under (c) and (d) above. Among such compounds, the $R^3$ and $R^4$ and $R^5$ and $R^6$ groups for the ethers and esters, respectively, can be either acyclic or cyclic. The cyclic $R^3$, $R^4$, $R^5$, and $R^6$ groups are preferably saturated and can be either straight-chain or branched-chain groups. Preferably, the acyclic $R^3$, $R^4$, $R^5$, $R^6$ groups are straight-chain groups. The cyclic $R^3$, $R^4$, $R^5$, and $R^6$ groups can be either saturated cycloaliphatic groups or aromatic groups. However, if either $R^3$, $R^4$ and $R^5$ or $R^6$ contains an aromatic group, the aromatic group will be attached to a saturated aliphatic group of from 1 to 13 carbon atoms and the saturated aliphatic group will be attached to the oxygen atom in the ether or ester functional groups, as, for example, dibenzyl ether, benzyl acetate, methyl p-toluate, and the like. The cyclic $R^3$, $R^4$, $R^5$, and $R^6$ groups can contain aliphatic substituents anywhere on the ring. Usually, the aliphatic substituents will be alkyl hydrocarbon groups. Where $R^3$, $R^4$, $R^5$, and $R^6$ are oxygenated hydrocarbon groups, $R^3$, $R^4$, $R^5$, and $R^6$ can contain additional ether groups

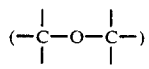

and carbonyl groups

and carboxy groups

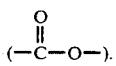

In addition, cyclic ether and cyclic ester compounds, wherein the hydrocarbyl group are saturated hydrocarbon alkylene groups having from 3 to 12 carbon atoms, are also suitable for use as the carbonylatable reactant. Such hydrocarbon alkylene groups can contain various cyclic and acyclic hydrocarbon substituents, although, in general, the substituent will be alkyl hydrocarbon groups anywhere on the ring structure.

Non-limiting examples of suitable ether carbonylatable reactants defined under (c) above include dimethyl ether, diethyl ether, methyl ethyl ether, diisobutyl ether, dioctyl ether, methyl decyl ether, dibenzyl ether, methyl benzyl ether, bis[3-methylbenzyl ether, diglyme [bis(2-methoxyethyl) ether, diethylene glycol dimethyl ether], glyme (1,2-dimethoxyethane, ethylene glycol dimethyl ether), 1,4-butanediol dibutyl ether, methoxyacetone, tetrahydrofuran, 2-octyltetrahydrofuran, dicyclohexyl ether, cyclohexyl ethyl ether, methyl isobutyl ether, diisopropyl ether, and the like.

Non-limiting examples of suitable ester carbonylatable reactants defined under (d) above include methyl acetate, ethyl acetate, methyl propionate, ethyl propionate, benzyl acetate, methyl benzoate, pentaerythrityl tetraacetate, octyl nonanoate, decyl decanoate, cyclohexyl acetate, ethyl cyclohexanecarboxylate, $\gamma$-butyrolactone, $\gamma$-valerolactone, caprolactone, 1,4-butanediol diacetate, benzyl benzoate, diethyl adipate, ethyl acetoacetate, 2-methylcycloheptyl acetate, methyl p-toluate, and the like.

Suitable olefinic carbonylatable reactants are those which correspond to the olefins defined under (e) above and include ethylene, propylene, the butenes, hexenes, oxtenes, hexadiene, 2-methylpropene, 1,3-butadiene, 2-methyl-1,3-butadiene, 2,3-dimethyl-1,3-butadiene, cyclohexene, 3,3-dimethyl-1-butene, 1,4-hexadiene, 2,4-hexadiene, 1,5-hexadiene, 2-methyl-1,4-hexadiene, acrolein, methyl vinyl ketone, 2-phenyl-2-butene, cyclopentadiene, 2-cyclohexyl-1-butene, 1,5-cyclooctadiene, 1,5,9-cyclododecatriene, cholesterol, progesterone, $\alpha$-pinene, limonene, and the like.

The carbonylation reaction may be carried out by intimately contacting the carbonylatable reactant which, depending upon the carbon number and operating conditions, may either be in the vapor or liquid phase, with gaseous carbon monoxide in a liquid reaction medium containing the catalyst system of the instant invention to form the carbonylation product. The particular conditions selected are the same whether the carbonylatable reactant is charged as a vapor or liquid. The temperature will be in the range of 50° C. to 400° C., with the preferred range being 100° C. to 240° C. and a more preferred range being about 100° C. to 190° C. Partial pressures of carbon monoxide on the order of 6.893 kPa-G to $1.034 \times 10^5$ kPa-G (1 psig to 15,000 psig) may be employed. However, carbon monoxide partial pressure from about 34.5 kPa-G to $2.068 \times 10^4$ kPa-G (5 psig to 3,000 psig) is generally preferred, with a more preferred range being from 68.9 kPa-G to $6.89 \times 10^3$ kPa-G (10 psig to 1,000 psig). Higher pressures, however, may be used, if desired, under appropriate conditions. However, such higher pressures are rarely used because the use of the catalyst system of the instant invention permits high reaction rates with good product yields to be obtained by operating at much lower pressures without any danger of catalyst decomposition, thus providing important economic advantages over prior art catalysts and methods for producing carbonylation products. As an example, the carbonylation reaction of ether and ester carbonylatable reactants such as dimethyl ether and methyl acetate, respectively, (under substantially anhydrous conditions as hereinafter described) consistently produces a yield of acetic anhydride (as the carbonylation product) of greater than about 50% by weight of product.

Alternatively, the carbonylation products may be produced, if desired, via reaction of a carbonylatable reactant with carbon monoxide (and water where water is a desirable reactant such as, for example, when the desired carbonylation product is a carboxylic acid) in the vapor phase over the catalyst system of the instant invention dispersed upon an inert solid support. Such a catalyst system may be operated as a conventional fixed bed catalytic reactor. For example, methyl acetate, methyl iodide, and carbon monoxide in the vapor phase may be passed over the catalyst system in solid form in a fixed bed reactor maintained at elevated temperature and pressure, as previously described, to produce acetic acid (in the presence of sufficient water) and/or acetic anhydride (in the absence of water) or mixtures thereof, depending upon the amount of water present, all in high yields. It is preferred, however, to employ the catalyst system of the instant invention as a solution or dispersion in the liquid phase.

While any amount of carbon monoxide may be employed in carbonylation reactions using the catalyst system of the instant invention, typical carbonylation reactions require at least 1 mole of carbon monoxide per mole of alcohol, ester, halide, and olefin carbonylatable reactants and at least 2 moles of carbon monoxide per mole of ether carbonylatable reactant. It will be understood, however, that the actual amount of carbon monoxide required to carry out the carbonylation reaction will depend upon the carbonylatable reactant as well as the desired carbonylation product. An excess of carbon monoxide over the required stoichiometric amounts, however, may also be employed. Carbon monoxide streams containing inert impurities such as carbon dioxide, methane, nitrogen, noble gases, paraffinic hydrocarbons having from 1 to 4 carbon atoms, may be employed, if desired, such as that from an available plant gas stream, with no adverse effect. In such cases, however, total reactor pressure will have to be increased to maintain a desired carbon monoxide partial pressure. The concentration of carbon monoxide in the feed gas stream is from 1 volume percent to 100 volume percent. Preferably, the concentration of the carbon monoxide in the feed gas stream should be in excess of 10 volume percent.

In addition to the above-mentioned inert impurities, the carbon monoxide feed gas stream may also contain hydrogen as a component in noninterfering amounts. Such moninterfering amounts of hydrogen will vary, depending upon the carbonylatable reactant and upon the desired carbonylation product. As an example and as indicated in Table 1 below, the presence or absence of hydrogen in the feed gas stream has little or no effect on the carbonylation product distribution during the carbonylation of alcohols to produce carboxylic acids. This has been found to be especially true for the carbonylation of methanol to produce acetic acid. The presence of large amounts of hydrogen, however, should be avoided since it unnecessarily causes an increase in the reactor system pressure in order to maintain a desired carbon monoxide partial pressure. On the other hand, noninterfering amounts of hydrogen in the feed gas stream may, in many instances, be beneficial as an aid in maintaining catalyst activity, particularly during the use of the preferred iodide promoter.

The term "noninterfering amount of hydrogen" is employed herein to mean any amount of hydrogen which can be present in the carbon monoxide feed gas stream without causing an adverse effect upon either the course of the carbonylation reaction or upon the carbonylation product yield.

As previously noted, water may be present or absent during the carbonylation reaction, depending upon the carbonylation products desired. When an alcohol, ester, ether, halide, or olefin is the carbonylatable reactant and the carbonylation product desired is the corresponding carboxylic acid, it is in general advantageous to include water in an amount sufficient to produce such carboxylic acid. Normally, in order to insure complete hydrolysis to the carboxylic acid, an equimolar or equivalent amount of water (based on the number of carbonylation sites present in the carbonylation reactant) is charged to the reaction system, although more or less water may be employed. As an example, when an ester is the carbonylatable reactant and the carbonylation product is the corresponding carboxylic acid, the reaction system, as previously noted is charged with an equimolar amount of water (based on the number of moles of ester present), although more or less water may be employed. An amount of water in excess of the equimolar quantity of water to carbonylatable reactant, for example, an excess equal to 50% to 300% of such equimolar quantity, already present with such carbonylatable reactant, promotes the production of carboxylic acids.

On the other hand, when carboxylic acid anhydrides are the desired carbonylation product, especially when esters and/or ethers are employed as the carbonylatable reactant, water (as well as alcohols) has an adverse effect on the carbonylation reaction with respect to the carbonylation product obtained. If less than equimolar amounts of water are present, then some anhydride will be produced, the actual amount of anhydride produced being dependent upon the extent of the reduction of water below the equimolar amount. However, in order to produce the maximum yield of carboxylic acid anhydride from esters and/or ethers, the carbonylation reaction must be carried out under substantially anhydrous conditions. That is, the carbonylatable reactants, as well as the carbon monoxide stream should be substantially free of water. In addition, alcohols, which contain hydroxyl groups (as well as other hydroxylic material) may also exert a detrimental effect on the production of the desired carboxylic acid anhydride product in that the presence of alcohols in the absence of water favors the production of esters. It will be understood, of course, that in those instances when a halide or an olefin is employed as the carbonylatable reactant, the presence of one or more hydroxylic species, depending on the carbonylation product desired, is necessary in order to complete the reaction. For example, in the carbonylation of olefins to produce carboxylic acid anhydrides, one mole of water is required for each two moles of olefin reacted or for each mole of carboxylic acid anhydride produced.

Any conventional method for drying suitable carbonylatable reactants can be employed to provide substantially anhydrous carbonylatable reactants and carbon monoxide gas streams. If the carbonylatable reactants which do not require the presence of a hydroxylic species to complete the reaction (other than alcohols) contain alcohols as a contaminant, steps should be taken to remove the alcohol contaminant from such carbonylatable reactants in those instances wherein the desired carbonylation product is the carboxylic acid anhydride.

The term "substantially anhydrous", as employed herein, means not more than 0.05 mole of water per mole of total carbonylatable reactant present in the carbonylation reactor.

The actual carbonylation product produced using the catalyst system of the instant invention varies depending upon the carbonylatable reactant and the presence or absence of other reactants in the reaction medium. As an example, consider the reaction of a carboxylic ester as the carbonylatable reactant. In the absence of water, the principal carbonylation product is the carboxylic acid anhydride. If water is present, then the carboxylic acid is produced, the amount being dependent upon the amount of water present. That is, if an equimolar or equivalent amount or more of water is present, the carboxylic acid is the major carbonylation product. The carbonylation product produced from other suitable carbonylatable reactants, for example, alcohols, halides, ethers, and/or olefins, in a similar manner depends upon the presence or absence of other reactants.

As another example, consider the reaction of an alcohol having n carbon atoms as the carbonylatable reactant where n is an integer from 1 to 20. In the presence of a carboxylic acid having n+1 carbon atoms, and/or the ester of the carboxylic acid and the alcohol, the carbonylation product is dependent upon the mole ratio of such materials, which ratios may vary from 0.001 to 10,000. The use of an alcohol/ester-containing reaction medium in which the alcohol/ester mole ratio is less than 2/1, preferably 0.001/1 to 2/1 (including pure ester) yields a carbonylation product with a high proportion of carboxylic acid, for example, reaching substantially 100% carboxylic acid. Alternatively, the use of an alcohol/ester mole ratio greater than 10/1, preferably 10/1 to 10,000/1 (including pure alcohol) tends to yield a carbonylation product with a very high proportion of the ester, for example, reaching substantially 100% ester.

Within this latter alcohol/ester mole ratio range of

The preferred mole ratio range for high ester production is an alcohol/ester mole ratio in the reaction medium of 10/1 to 10,000/1. The preferred mole ratio range for high carboxylic acid production is an alcohol/ester mole ratio of 0.001 to 2/1.

The various carbonylation products produced using the catalyst system of the instant invention are summarized in Table 1.

TABLE 1

| CARBONYLATABLE REACTANT | CARBONYLATION PRODUCT/CONDITIONS | | | |
|---|---|---|---|---|
| | WATER | | HYDROGEN | |
| | ABSENT | PRESENT | ABSENT | PRESENT |
| Alcohol | Carboxylic Acid/ Carboxylic Acid Ester[1] | Carboxylic Acid/ Carboxylic Acid Ester[1] | Carboxylic Acid/ Carboxylic Acid Ester[1] | Carboxylic Acid/ Carboxylic Acid Ester[1] |
| Halide | Acyl Halide[2] | Carboxylic Acid | Carboxylic Acid[3] Carboxylic Acid Ester[4] Carboxylic Acid Anhydride[5] | Carboxylic Acid[3] Aldehyde Carboxylic Acid Ester[4] Carboxylic Acid Anhydride[5] |
| Ester | Carboxylic Acid Anhydride | Carboxylic Acid | Carboxylic Acid Anhydride[6] | |
| Ether | Carboxylic Acid Anhydride Carboxylic Acid Ester | Carboxylic Acid | Carboxylic Acid Anhydride[6] | |
| Olefin | Olefin-Catalyst Complex Carboxylic Acid Anhydride[7] Carboxylic Acid Ester[4] | Carboxylic Acid Carboxylic Acid Anhydride[8] | — | Aldehyde[6] Alkane |

[1]Relative amounts of carboxylic acid/carboxylic acid ester affected by the amount of water present, and, if carboxylic acid ester is present, the alcohol/ester mole ratio and conversion level.
[2]Speculated to be present; not actually identified.
[3]If water is present.
[4]If alcohol is present.
[5]If carboxylic acid is present and water is present in less than stoichiometric amounts.
[6]In the absence of water.
[7]If carboxylic acid is present.
[8]One mole of water is required for each two moles of olefin reacted or for each mole of carboxylic acid anhydride produced.

10/1 to 10,000/1, there exist two alternative modes of operation. In the first such mode, the product consists essentially of 100% ester at alcohol conversion levels up to about 90 mole percent. In the second such mode, the alcohol conversion level exceeds about 90 mole percent in which instance the carbonylation product is substantially completely the carboxylic acid. Within the alcohol/ester mole ratio range of 2/1 to 10/1 within the reaction medium, the relative proportions of acid and ester in the product may be controlled. As the ester concentration goes down, the ester production goes up, subject to the conversion level as previously indicated.

The above cases are summarized below.

| Alcohol/Ester Mole Ratio in Reaction Medium | Major Product |
|---|---|
| 0.001 to 2/1 | Carboxylic Acid |
| 2/1 to 10/1 | Mixed Carboxylic Acid and Ester |
| 10/1 to 10,000/1 | |
| (a) To about 90% alcohol conv. | Carboxylic Acid Ester |
| (b) Above about 90% alcohol conv. | Carboxylic Acid |

The desired carboxylic acid of n+1 may be present in the reaction mixture, e.g., as solvent. This acid will readily esterify, and the control of the product distribution previously described is applicable, with the alcohol/ester mole ratio being the controlling factor.

The reaction rate is dependent upon catalyst concentration and temperature. Concentrations of the rhodium-containing catalytically active component of the catalyst system in the liquid phase between $10^{-6}$ mole/liter and $10^{-1}$ mole/liter, are normally employed, with the preferred range being $10^{-4}$ mole/liter to $10^{-2}$ mole/liter. Higher concentrations, even to the extent of 1 mole/liter, may, however, be employed if desired. Higher temperatures also favor higher reaction rates.

The concentration of the halogen-containing promoter component based on halogen atoms, may vary widely, subject only to the requirement that the halogen must be present in an amount sufficient to provide an excess of halogen atoms over the rhodium atoms and practical considerations.

The catalyst system of the instant invention, as previously noted, is preferably supplied as a catalyst system solution, which can also include liquid carbonylatable reactants, carbonylation products, and mixtures thereof which function as solvent or reaction media to enhance and maintain catalyst solubility, improve production of the desired carbonylatable products and facilitate overall efficiency of the carbonylation reaction using the catalyst system of the instant invention. Such catalyst system solutions are therefore essentially comprised of (1) the carbonylatable reactant-carbonylation product medium, (2) a rhodium-containing catalytically active component, and (3) a halogen-containing promoter component, the halogen being selected from the group consisting of bromine, iodine, bromide compounds, and iodide compounds.

In one embodiment of the use of the catalyst system of the instant invention, a high-boiling, inert solvent such as tri-n-butylamine as previously described, together with the catalyst system of the instant invention, is employed. This embodiment is particularly suitable for use with a gas-sparged reactor system wherein the feed is a liquid such as dimethyl ether and the carbon monoxide is introduced in gaseous form. The carbonylation product stream is removed from the reactor as a vapor containing carbonylation product, for example, acetic anhydride. In this embodiment, no liquid is withdrawn so that a distinct advantage exists because of the elimination of catalyst handling, thus minimizing catalyst losses. The vapor stream leaving the reactor is then condensed and the carbonylation product can be recovered from the liquid condensate by distillation.

The catalyst system of the instant invention when used in carbonylation reactions is characterized by an unusually high degree of specificity for the carbonylation product. Such control over the various competing reactions to obtain the carbonylation product in high yield is surprising since other metal catalysts do not show such specificity. The iron group metals such as iron, cobalt, and nickel differ from the instant catalyst system in that the iron group metals simultaneously produce large amounts of undesirable by-products. Furthermore, the iron group catalysts, particularly cobalt, require a far higher carbon monoxide partial pressure to remain stable. When moderate pressures, for example, less than about $1.38 \times 10^4$ kPa-G (2000 psig) carbon monoxide pressures are employed, at a temperature of 175° C., the cobalt catalyst is found to plate out or decompose to the free metal which plates on the walls of the reactor and is therefore lost as a catalyst.

The catalyst system of the instant invention may be employed in carbonylation reactions operated either as a batch or as a continuous process. In batch operations, the reactants are charged into the reactor that contains either the solid supported catalyst system or the liquid catalyst system solution, which is then subjected to the desired temperature and pressure conditions, after which the products are separated from the reaction mixture. In a continuous mode of operation, the catalyst system is maintained in a liquid state or supported on a suitable support material with the reactants being continuously supplied to the reaction zone containing the catalyst system at the desired temperature and pressure. The products are continuously withdrawn, either in the vapor state or as previously described by withdrawing a vapor product or a portion of the solution containing the catalyst system, unreacted feed materials, equilibrium components, and the desired carbonylation product. The desired carbonylation product is then separated from such solution to permit recycling of the catalyst system-containing solution, unreacted feed, and also equilibrium components. In general, it is preferred, particularly on a commercial scale, to carry out such carbonylation reactions in a continuous mode.

The reactor used to carry out carbonylation reactions, regardless of whether a liquid catalyst system solution or a solid supported catalyst system is employed, can be constructed of any suitable corrosion resistant material. When the preferred liquid reaction medium is employed, the reactor can be equipped with a gas-sparger below the surface of the liquid reaction mixture. Carbon monoxide can be bubbled into the liquid reaction mixture continuously. The carbon monoxide bubbling through the reaction mixture provides some degree of agitation but in most instances it will be desirable to mechanically agitate the reaction mixture with paddle wheels and the like to obtain the desired contact between the carbon monoxide and the liquid phase.

In most instances it is desired, as previously noted, to also add an additional solvent or stabilizing component such as tri-n-butylamine to the reaction mixture. A small amount of the reaction mixture can be intermittently or continuously withdrawn from the reactor and passed to a separation zone. The separation zone can be a conventional simple distillation column wherein the carbonylation product can be vaporized from the reaction mixture along with any unreacted feed materials such as dimethyl ether and other volatile materials. The remaining liquid phase, containing the catalyst system of the instant invention can then be recycled to the reactor. In some instances it may be desirable to utilize a flash tank for separating the carbonylation product and the unreacted reactants from the reaction mixture. This can be conveniently accomplished by withdrawing a portion of the reaction mixture from the reactor and passing it to a zone of reduced pressure either with or without the addition of heat, thus causing the carbonylation product and the unreated feed components and volatile materials to vaporize, leaving the catalyst system contained in the unvaporized liquid in the flash tank. The liquid in the flash tank can then be recycled to the reactor. It is, of course, understood that the carbonylation product can be further purified by conventional purification techniques known to the art.

The carbonylation products produced during the course of the carbonylation reaction using a solid supported catalyst system can be collected in a suitable chilled container, that is, by condensation. The condensed liquid can then be purified in the same manner described for the carbonylation products produced via liquid phase carbonylation reactions.

The following specific examples illustrating the best presently known method of practicing this invention are described in detail in order to facilitate a clear understanding of the invention. It should be understood, however, that the detailed expositions of the application of the invention while indicating preferred embodiments are given by way of illustration only and are not to be construed as limiting the invention since various changes and modifications within the spirit of the invention will become apparent to those skilled in the art from this detailed description.

EXAMPLE 1

A batch reactor was charged with 0.396 g (0.0015 mole) of a rhodium compound having the formula $RhCl_3.3H_2O$, 28.8 g (0.20 mole) of a promoter consisting of methyl iodide, $CH_3I$, 196.9 g (3.28 moles) of acetic acid as a solvent, and 79.0 g (2.47 moles) of methanol as carbonylatable reactant or feedstock. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig), at the reaction temperature of 175° C. The reaction was carried out at a constant pressure to yield a solution containing the following distribution of products:

89.0 wt % Acetic Acid
3.6 wt % Methyl Iodide 8.4 wt % (Catalyst, etc.)

The selectivity to the formation of the desired acetic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 335 minutes. The present experiment as well as the other examples, was carried out at a slow rate in order to permit a study of the mechanism of the reaction. However, when the rates were increased to those of a commercial unit, high selectivity and conversions were also obtained.

EXAMPLE 2

A batch reactor was charged with 1.037 g (0.0015 mole) of a rhodium complex (coordination compound) having the formula $Rh(CO)Cl[(C_6H_5)_3P]_2$, 28.8 g (0.20 mole) of a promoter consisting of methyl iodide, $CH_3I$ (ratio of promoter halogen to rhodium atoms about 133.3/1), 196.9 g (3.28 moles) of acetic acid as a solvent, and 79.0 g (2.47 moles) of methanol as carbonylatable reactant or feedstock. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig), at the reaction temperature of 175° C. The reaction was carried out at a constant pressure to yield a solution containing the following distributionn of products:

96.83 wt % Acetic Acid
1.29 wt % Methyl Iodide
1.88 wt % (Catalyst, etc.)

Selectivity to the formation of the desired carboxylic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 155 minutes.

This example demonstrates the effect of the use of a rhodium complex as the catalyst source instead of a simple rhodium salt as compared with Example 1.

. EXAMPLE 3

This example demonstrates the ability to carry out the reaction in the presence of the feedstock (carbonylatable reactant) as a solvent.

A batch reactor was charged with 0.396 g (0.0015 mole) of a rhodium compound having the formula $RhCl_3.3H_2O$, 57.5 g (0.40 mole) of a promoter consisting of $CH_3I$, and 217.0 g (6.78 moles) of methanol feedstock. The reactor was pressurized with carbon monoxide to a total pressure of $6.893 \times 10^3$ kPa-G [1,000 psig, partial pressure of carbon monoxide about $4.82 \times 10^3$ kPa-G (700 psig)]at the reaction temperature of 175° C. The reaction was carried out at a constant pressure to yield a solution containing the following distribution of products:

81.9 wt % Acetic Acid
3.2 wt % Methyl Iodide
14.2 wt % (Catalyst, etc.)

Selectivity to formation of the carboxylic acid product was greater than 95% at substantially 100% methanol conversion. No undesirable by-products such as aldehydes, dimethyl ether, higher boiling carboxylic acids, methane, carbon dioxide, etc., were detected by gas chromatography. The time required for 50% of the methanol to be converted to acetic acid was 270 minutes.

This example uses a promoter ratio (atoms of promoter halogen per atom of rhodium) of about 266.6/1. However, it was found that the use of lower ratios such as 200/1, as well as still lower ratios, such as 10/1 gave similar results.

EXAMPLE 4

This example demonstrates the use of an inert solvent. A batch reactor was charged with 0.396 g (0.0015 mole) of the rhodium compound having the formula $RhCl_3.3H_2O$, 57.5 g (0.40 mole) of promoter consisting of $CH_3I$, 154.0 g (1.97 moles) of benzene as solvent, and 79.0 g (2.47 moles) of methanol feedstock. The reactor was pressurized with carbon monoxide to a total pressure of $6.893 \times 10^3$ kPa-G [1,000 psig, $5.17 \times 10^3$ kPa-G (750 psig) partial pressure of carbon monoxide] at the reaction temperature of 175° C. The reaction was carried out at constant pressure to yield a solution containing the following distribution of products on a solvent-free basis:

62.9 wt % Acetic Acid
5.0 wt % Methyl Acetate
32.1 wt % Methyl Iodide

Selectivity to formation of the carboxylic acid product was greater than 90% at substantially 100% methanol conversion. The methyl acetate which was produced in the reaction was in equilibrium with the various reactants and products, and exerted no deleterious effect on the catalytic reaction system. In a continuous operation, the methyl acetate attains an equilibrium concentration, so that the methyl acetate removed during product separation steps is recycled to the reactor system. Consequently, no yield or selectivity losses occur due to the presence and formation of undesirable by-products such as aldehydes, higher alcohols, dimethyl ether, higher ether, higher boiling carboxylic acids. No methane or carbon dioxide were detected by gas chromatography. The time required for 50% of the methanol to be converted to acetic acid was about 300 minutes. The ratio of alcohol to ester in the feedstock in this example was about 10,000 (which corresponds to a substantially pure methanol feedstock) even in the presence of benzene as an inert solvent. Also, the conversion level of the methanol feedstock was greater than 90%. In accordance with the alcohol/ester mole ratio criteria, the product of this reaction was substantially completely acetic acid.

EXAMPLE 5

This example demonstrates that a compound of rhodium in complex combination with triphenylphosphine in an inert solvent and in the presence of additional triphenylphosphine ligand is a reactive catalyst.

A batch reactor was charged with 1.04 g (0.0015 mole) of a rhodium complex having the formula $[(C_6H_5)_3P]_2RhCOCl$, 19.6 g (0.0075 mole) of triphenylphosphine ligand, $(C_6H_5)_3P$, 57.5 g (0.40 mole) of a promoter consisting of $CH_3I$, 154.0 g (1.97 moles) of benzene as solvent, and 79.0 g (2.47 moles) of methanol feedstock. The reactor was pressurized with carbon monoxide to a total pressure of $6.893 \times 10^3$ kPa-G, [1,000 psig, carbon monoxide partial pressure about $5.17 \times 10^3$ kPa-G (750 psig)] at the reaction temperature of 175° C. The reaction was carried out at constant pressure to yield a solution containing the following distribution of products (exclusive of solvent):

86.4 wt % Acetic Acid 15.4 wt % Methyl Iodide

Selectivity to formation of the carboxylic acid product was greater than 95% at substantially 100% conversion of methanol. No substantial amounts of by-products such as aldehydes, dimethyl ether, higher boiling carboxylic acid, methane and carbon dioxide were detected by gas chromatography. The time required for 50% of the methanol to be converted to acetic acid was 85 minutes.

EXAMPLE 6 (COMPARATIVE)

This example demonstrates that cobalt carbonyl is a far less effective catalyst system than the present catalyst system of rhodium compounds. A batch reactor was charged with 2.58 g (0.0075 mole) of dicobalt octacarbonyl, 28.8 (0.20 mole) of a promoter consisting of $CH_3I$, 165.0 g (2.12 moles) of benzene as solvent, and 79.0 g (2.47 moles) of methanol feedstock. The reactor was initially pressurized with carbon monoxide to a total pressure of $6.893 \times 10^3$ kPa-G [1,000 psig, $5.17 \times 10^3$ kPa-G (750 psig) carbon monoxide partial pressure] at the reaction temperature of 175° C. The reaction was carried out at a constant pressure. More than 50 mole % of the methanol feedstock was converted to dimethyl ether. Water and a trace amount of methyl acetate were also produced. No acetic acid was obtained.

When this test was repeated using a platinum triphenylphosphine catalyst, i.e., $Pt[P(C_6H_5)_3]$, no reaction occurred.

EXAMPLE 7 (COMPARATIVE)

This example demonstrates that cobalt salts are relatively poor catalysts for the production of acetic acid from methanol even when higher pressures of carbon monoxide and higher temperatures are employed. A batch reactor was charged with 1.57 g (0.0063 mole) of $Co(C_2H_3O_2)_2 \cdot 4H_2O$, 3.81 g (0.030 mole) of iodine as a promoter, and 237.0 g (7.41 moles) of methanol feedstock (carbonylatable reactant). The reactor was initially pressurized with carbon monoxide to a total pressure of $1.72 \times 10^4$ kPa-G [2,500 psig, $1.38 \times 10^4$ kPa-G (2,000 psig) carbon monoxide partial pressure] at the reaction temperature of 195° C. Rapid decomposition of the cobalt catalyst to cobalt metal (plating out) occurred. Analysis of the reaction mixture showed that more than 60 mole % of the methanol feedstock was converted to dimethyl ether. A considerable amount of water was also produced, and less than 5 mole % of the methanol feedstock was converted to methyl acetate and acetic acid.

EXAMPLE 8

This example demonstrates the ability to use the product as a solvent for the reaction without any deleterious effects on the rate of the reaction of product distribution.

A batch reactor was charged with 1.037 g (0.0015 mole) of a rhodium compound having the formula $[(C_6H_5)_3P]_2Rh(CO)Cl$, 19.6 g (0.075 mole) of additional triphenylphosphine, 28.8 g (0.20 mole) of a promoter consisting of methyl iodide, 196.9 g (3.28 moles) of acetic acid as solvent, and 79.0 g (2.47 moles) of methanol feedstock. The reactor was pressurized with carbon monoxide to a total pressure of $6.893 \times 10^3$ kPa-G [1,000 psig, $5.51 \times 10^3$ kPa-G (800 psig) partial pressure of carbon monoxide] at the reaction temperature of 175° C. The reaction was carried out at constant pressure to yield a solution containing the following distribution of components as determined by gas chromatography:

88.5 wt % Acetic Acid 1.5 wt % $CH_3I$ 10.0 wt % (Catalyst, etc.)

No methanol or methyl acetate was detected. The selectivity to formation of carboxylic acid product was greater than 95% at substantially 100% methanol conversion. No undesirable by-products such as aldehydes, dimethyl ether, higher boiling carboxylic acid, methane, carbon dioxide, etc., were detected by gas chromatography. The time required for 50% of the methanol to be converted to acetic acid was 150 minutes.

EXAMPLE 9

This example and the following example, Example 10, demonstrate the effect of partial pressure of carbon monoxide on the reactions.

This example is similar to Example 8 except that the reactor was pressurized with carbon monoxide to a total pressure of $1.38 \times 10^4$ kPa-G [2,000 psig, about $1.24 \times 10^4$ kPa-G (1,800 psig) carbon monoxide partial pressure] at the reaction temperature of 175° C. The time for 50% of the methanol to be converted to acetic acid was 190 minutes. The composition of the resulting reaction solution, as determined by gas chromatography, is shown below:

90.4 wt % Acetic Acid 9.6 wt % (Catalyst, etc.)

Only a trace amount of methyl iodide and no methanol or methyl acetate was detected. Also, no undesirable by-products such as aldehydes, dimethyl ether, higher boiling carboxylic acids, methane, carbon dioxide, etc., were detected.

EXAMPLE 10

A batch reactor was charged with 1.04 g (0.0015 mole) of a rhodium compound having the formula $[(C_6H_5)_3P]_2RhCOCl$, 1.23 g (0.0047 mole) of additional triphenylphosphine as a ligand, 28.8 g (0.20 mole) of a promoter consisting of methyl iodide, 196.9 g (3.28 moles) of acetic acid as solvent, and 79.0 g (2.47 moles) of methanol feedstock. The reactor was pressurized with carbon monoxide to a total pressure of $3.45 \times 10^3$ kPa-G [500 psig, about $2.068 \times 10^3$ kPa-G (300 psig) carbon monoxide partial pressure] at the reaction temperature of 175° C. The reaction was carried out at constant pressure to yield a solution containing the following distribution of components, as determined by gas chromatography:

90.0 wt % Acetic Acid 3.9 wt % Methyl Iodide 6.1 wt % (Catalyst, etc.)

No methanol or methyl acetate was detected. Selectivity to formation of the carboxylic acid product was greater than 95% at substantially 100% methanol conversion. No undesirable by-products such as aldehydes, dimethyl ether, higher boiling carboxylic acids, methane, carbon dioxide, etc., were detected by gas chromatography. The time required for 50% of the methanol to be converted to acetic acid was 150 minutes.

This example demonstrates that the use of a carbon monoxide partial pressure as low as $2.068 \times 10^3$ kPa-G (300 psig) gives results similar to those obtained at the higher partial pressure of carbon monoxide employed, for example, in Examples 8 and 9.

The alcohol/ester mole ratio in the feedstock in Examples 8, 9 and 10 was about 0.001 (which corresponds to a substantially pure methyl acetate feedstock) in the presence of acetic acid as solvent. The acetic acid solvent and methanol feedstock readily esterify. In accordance with the alcohol/ester mole ratio criteria, the ratio of alcohol to ester was a controlling factor in product distribution. Consequently, the product of this reaction was substantially completely acetic acid.

EXAMPLE 11

This example demonstrates that an increase in temperature increases the reaction rate.

This example is similar to Example 9 except that the reaction temperature was 200° C. The composition of the resulting reaction solution was substantially the same as that of Example 9. The time required for 50% of the methanol to be converted to acetic acid was 80 minutes as compared with 190 minutes in Example 9 at a temperature 25° lower, i.e., 175° C.

EXAMPLE 12

This example demonstrates that the reaction may be carried out in the presence of hydrogen without the formation of undesirable products such as acetaldehyde and/or ethanol and without catalyst decomposition. This example is similar to Example 5 above, except that the reaction was carried out in an atmosphere of 62 vol. % carbon monoxide and 38 vol. % of hydrogen corresponding to a synthetic gas mixture at a total pressure of $1.38 \times 10^4$ kPa-G [2,000 psig, $7.58 \times 10^3$ kPa-G (1,100 psig) partial pressure of carbon monoxide]. The selectivity to formation of the acetic acid product was greater than 95% at substantially 100% conversion of methanol. No substantial amounts of reduced materials or other by-products such as aldehydes, dimethyl ether, ethanol, higher boiling carboxylic acids, methane, carbon dioxide, etc., were detected by gas chromatography, thus distinguishing from cobalt catalyst which yield such by-products as the result of hydrogenation catalyzed by the cobalt. The time required for 50% of the methanol to be converted to acetic acid was 83 minutes.

A similar result was obtained with another synthetic gas mixture, e.g., a 66 vol. % hydrogen, 33 vol. % carbon monoxide, such as is obtained from a commercial unit. The various impurities, e.g., nitrogen, hydrogen, carbon dioxide and paraffinic hydrocarbons of 1 to 4 carbon atoms, which are present in such feed gas mixtures, did not adversely affect the present reaction.

EXAMPLE 13

This example demonstrates the effect of the rate of reaction as a function of the concentration of the halogen-containing promoter component. This example is similar to Example 5 above, except that only 28.8 g (0.20 mole) of methyl iodide promoter was added. The selectivity to formation of carboxylic acid product was greater than 95% at substantially 100% conversion of methanol. No substantial amounts of by-products such as aldehydes, dimethyl ether, higher boiling carboxylic acid, methane, carbon dioxide, etc., were detected by gas chromatography. The time required for 50% of the methanol to be converted to acetic acid was 198 minutes as compared with 85 minutes in Example 5 when twice as much promoter was used.

The alcohol/ester mole ratio in the feedstock in Examples 12 and 13 was about 10,000 (which corresponds to a substantially pure methanol feedstock) even in the presence of benzene as an inert solvent. Also, the conversion level of the methanol feedstock was greater than 90%. Accordingly, the carbonylation product of this reaction was substantially completely acetic acid.

EXAMPLE 14

A batch reactor was charged with 0.636 g (0.0013 mole) of a rhodium compound having the formula $RhI_3$, 78.8 g (0.55 mole) of a promoter consisting of methyl iodide, $CH_3I$, 196.9 g (3.28 moles) of acetic acid as a solvent, and 79.0 g (2.47 moles) of methanol as feedstock. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig), at the reaction temperature of 175° C. The reaction was carried out at a constant pressure to yield a solution containing the following distribution of products:

84.9 wt % Acetic Acid
3.8 wt % Methyl Iodide
11.3 wt % (Catalyst, etc.)

Selectivity to the formation of the desired carboxylic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 225 minutes.

This example demonstrates the effect of having the halogen-containing promoter partly charged with rhodium as rhodium iodide.

EXAMPLE 15

A batch reactor was charged with 1.037 g (0.0015 mole) of a rhodium complex having the formula $RhCOCl[P(C_6H_5)_3]_2$, 18.0 g (1.00 mole) of water, 33.6 g (0.20 mole) of a promoter consisting of potassium iodide, KI (I/Rh atom ratio about 133.3/1) 178.5 g (2.98 moles) of acetic acid as a solvent, and 79.0 g (2.47 moles) of methanol as feedstock. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig), at the reaction temperature of 175° C. The reaction was carried out at a constant pressure to yield a solution containing the following distribution of products:

89.6 wt % Acetic Acid
7.4 wt % Methyl Iodide
3.0 wt % (Catalyst, etc.)

Selectivity to the formation of the desired carboxylic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 137 minutes.

When potassium bromide, or hydrobromic acid at equivalent molar concentrations was used, a similar result was obtained. This example demonstrates the effect of using a bromide or iodide compound as the source of promoter halogen.

EXAMPLE 16

A batch reactor was charged with 1.17 g (0.0015 mole) of a rhodium compound having the formula $Rh(CO)Cl[As(C_6H_5)_3]_2$, 28.8 g (0.20 mole) of a promoter consisting of methyl iodide, $CH_3I$, 196.9 g (3.28 moles) of acetic acid as a solvent, and 79.0 g (2.47 moles) of methanol as feedstock. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig), at the reaction temperature of 175° C. The reaction was carried out at a constant pressure to yield a solution containing the following distribution of products:

97.1 wt % Acetic Acid
1.6 wt % Methyl Iodide
12.3 wt % (Catalyst, etc.)

Selectivity to the formation of the desired carboxylic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 166 minutes.

This example demonstrates the effect of triphenylarsine as a ligand as compared with Examples 1 and 2.

EXAMPLE 17

A batch reactor was charged with 1.038 g (0.0015 mole) of a rhodium compound having the formula $[(C_6H_5)_3P]_2Rh(CO)Cl$, 57.6 g (0.40 mole) of a promoter consisting of methyl iodide, $CH_3I$, 196.9 g (3.28 moles) of acetic acid as a solvent, and 79.0 g (2.47 moles) of methanol as feedstock. The reactor was pressurized with carbon monoxide to a total pressure of $2.76 \times 10^3$ kPa-G (400 psig), corresponding to a carbon monoxide partial pressure of about $8.96 \times 10^2$ kPa-G (130 psig), at the reaction temperature of 200° C. The reaction was carried out at a constant pressure to yield a solution containing the following distribution of products:

88.5 wt % Acetic Acid
6.8 wt % Methyl Iodide
4.7 wt % (Catalyst, etc.)

Selectivity to the formation of the desired carboxylic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 40 minutes.

EXAMPLE 18

A batch reactor was charged with 1.037 g (0.0015 mole) of a rhodium compound having the formula $Rh(CO)Cl[P(C_6H_5)_3]_2$, 28.8 g (0.20 mole) of a promoter consisting of methyl iodide, $CH_3I$, 178.5 g (2.98 moles) of acetic acid as a solvent, and 79.0 g (2.47 moles) of methanol as feedstock and 18.0 g (1.00 mole) water. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig) at the reaction temperature of 175° C. The reaction was carried out at a constant pressure to yield a solution containing the following distribution of products:

89.12 wt % Acetic Acid
0.56 wt % Methyl Iodide
10.32 wt % (Catalyst, etc.)

Selectivity to the formation of the desired carboxylic acid product was greater than 95% at substantially 100% conversion of methanol. No substantial amounts of by-products such as aldehydes, dimethyl ether, higher boiling carboxylic acids, methane, or carbon dioxide were formed. The time required for 50% of the methanol to be converted to acetic acid was 124 minutes.

This example demonstrates the beneficial effect upon the reaction rate of adding water to the reaction medium during the production of carboxylic acids as compared with Examples 2 and 15.

EXAMPLE 19

A batch reactor was charged with 0.396 g (0.0015 mole) of $RhCl_3.3H_2O$, 57.5 g (0.40 moles) of methyl iodide promoter (MeI) and 215.0 g of a methanol (MeOH) feedstock containing 10 wt % (21.5 g, 0.47 mole) dimethyl ether (MeOMe). The reactor was pressurized with carbon monoxide to a total pressure of $6.893 \times 10^3$ kPa-G (1,000 psig), corresponding to a carbon monoxide partial pressure of $4.82 \times 10^3$ kPa-G (700 psig), at the reaction temperature of 175° C. The reaction was carried out at a constant pressure until carbon monoxide take-up stopped, indicating completion of the reaction, to yield a product solution which upon analysis contained the distribution of components shown in the following table:

| Distribution wt % | Component | Principal Source |
|---|---|---|
| 78.20 | Acetic Acid (AcOH) | Carbonylation of MeOH |
| 9.18 | Methyl Iodide (MeI) | Feed Component |
| 9.46 | Acetic Anhydride ($Ac_2O$) | Carbonylation of $Me_2O$ |
| 2.69 | Methyl Acetate (MeOAc) | Carbonylation of $Me_2O$ and MeOH esterification of AcOH |
| 0.09 | Catalyst, etc. | Feed Component |
| 0.38 | Water ($H_2O$) | MeOH esterification of AcOH and/or intermolecular dehydration of MeOH to $Me_2O$ |

This example demonstrates that dimethyl ether in the substantial absence of water is carbonylated to acetic anhydride.

EXAMPLE 20

A batch reactor was charged with 1.037 g (0.0015 mole) of a rhodium compound having the formula $Rh(CO)Cl[P(C_6H_5)_3]_2$, 1.228 g (0.0047 mole) of additional triphenylphosphine ligand, 28.8 g (0.20 mole) of a promoter consisting of methyl iodide, $CH_3I$, 25.6 g (0.43 mole) of acetic acid, 36.8 g (2.044 moles) of water, 49.1 g (1.53 moles) of methanol, and 151.2 g (2.043 moles) of methyl acetate, which corresponds to the equilibrium concentrations of the ester and water components under the reaction conditions employed. The reactor was pressurized with carbon monoxide to a total pressure of $6.893 \times 10^3$ kPa-G (1,000 psig), corresponding to a carbon monoxide partial pressure of about $5.17 \times 10^3$ kPa-G (750 psig), at the reaction temperature of 175° C. The reaction was carried out at a constant volume until substantially all of the carbon monoxide had reacted [final reactor pressure about $1.7 \times 10^3$ kPa-G (250 psig), corresponding to substantially zero partial pressure of carbon monoxide because of the complete reaction of carbon monoxide].

The reaction product distribution which was obtained had substantially the same methyl acetate and water concentrations as initially charged; however, 60 wt % of the methanol charged to the reactor was converted to acetic acid.

No substantial amounts of by-products such as aldehydes, dimethyl ether, higher boiling carboxylic acids, methane or carbon dioxide were formed. The time required for substantially all of the carbon monoxide to be reacted with methanol and thus converted to acetic acid was 90 minutes which corresponds to a space-time yield (STY) of about 2.0 moles of product/liter of catalyst solution/hour. The rate of carbon monoxide conversion was changed by a factor of less than 2 over this total conversion range. It is also noted that the rate parameters of this, and the other examples were obtained when using a rate sufficiently low to permit a study of the reaction mechanism. However, when the rates were increased to those of a commercial unit, the same high selectivity and conversions were maintained.

This example demonstrates the concept of operating a continuous reactor to produce acetic acid from methanol while maintaining equilibrium recycle streams of the ester (methyl acetate) and water, and resulting in a net conversion of the methanol feedstock to the desired carbonylation product, acetic acid, while maintaining the stated equilibrium conditions.

EXAMPLE 21

A continuous reaction system was operated in which methanol and the equilibrium concentrations of methyl acetate and water were obtained from a commercial plant recycle system. The catalyst system, including the methyl iodide, and the feed mixture of Example 20, was continuously passed through a tubular reaction zone maintained at 175° C. to yield a result similar to that of Example 20. The use of a distillation separation train to recover unreacted methanol, and the equilibrium components methyl acetate and water, as well as the acetic acid product, permitted the recycling of the catalyst. Another product of the continuous reaction was the equilibrium mixture of methyl acetate and water, which also may be recycled.

EXAMPLE 22

A batch reactor was charged with 1.037 g (0.0015 mole) of rhodium compound having the formula $Rh(CO)Cl[P(C_6H_5)_3]_2$, 21.6 g (1.20 moles) of water, 28.8 g (0.20 mole) of a promoter consisting of methyl iodide, $CH_3I$, 89.0 g (1.20 moles) of methyl acetate, and 128.0 g (4.0 moles) of methanol as feedstock, which is equivalent to an alcohol/ester mole ratio of about 3.3. The reactor was pressurized with carbon monoxide to a total pressure of $3.45 \times 10^3$ kPa-G (500 psig), corresponding to a carbon monoxide partial pressure of about $1.72 \times 10^3$ kPa-G (250 psig), at the reaction temperature of 175° C. The reaction was carried out at a constant pressure to yield a solution having the following composition:

54.0 wt % Methyl Acetate
17.8 wt % Acetic Acid
3.6 wt % Methyl Iodide
15.3 wt % (Catalyst, etc.)
9.3 wt % Methanol Selectivity to the formation of the desired ester and acid product was about 98% at about 75% conversion of methanol. No substantial amounts of by-products such as aldehydes, dimethyl ether, higher boiling carboxylic acids, methane, and/or carbon dioxide were formed. The time required for the reaction was 135 minutes. The product distribution of the mixture of acid and ester products was in accordance with the criteria set forth herein for an alcohol/ester feed ratio in the range of 2 to 10. The reaction in this example resulted in a net production of 80.0 g (1.08 moles) of methyl acetate and 55.0 g (0.92 mole) of acetic acid.

EXAMPLE 23

A batch reactor was charged with 1.037 g (0.0015 mole) of a rhodium compound having the formula $Rh(CO)Cl[P(C_6H_5)_3]_2$, 28.8 g (0.20 mole) of a promoter consisting of methyl iodide, $CH_3I$, 72.0 g (1.20 moles) of acetic acid as a solvent, and 167.0 g (5.22 moles) of methanol as feedstock, which upon equilibration is equivalent to about the same alcohol/ester mole ratio of 3.3 as in Example 22. The reactor was pressurized with carbon monoxide to a total pressure of $3.45 \times 10^3$ kPa-G (500 psig), corresponding to a carbon monoxide partial pressure of about $1.72 \times 10^3$ kPa-G (250 psig), at the reaction temperature of 175° C. The reaction was carried out at a constant pressure to yield a solution containing substantially the same product distribution as in Example 22 under similar reaction conditions.

In accordance with the alcohol/ester mole ratio criteria set forth hereinabove, the carbonylation product distribution was controlled by the alcohol/ester mole ration after equilibration even when the initially charged feed contained organic acid and alcohol instead of the preformed ester of the two compounds. Consequently, the product distribution was a mixture of acid and ester products in accordance with the alcohol/ester mole ration range of 2 to 10.

EXAMPLE 24

A batch reactor was charged with 1.037 g (0.0015 mole) of a rhodium compound having the formula $Rh(CO)Cl[P(C_6H_5)_3]_2$, 28.8 g (0.20 mole) of a promoter consisting of methyl iodide, $CH_3I$, 30.0 g (0.50 mole) of acetic acid as a solvent, and 210.0 g (6.56 moles) of methanol as feedstock, which is equivalent to an alcohol/ester mole ratio of about 12 after equilibration. The reactor was pressurized with carbon monoxide to a total pressure of $3.45 \times 10^3$ kPa-G (500 psig), corresponding to a carbon monoxide partial pressure of about $1.72 \times 10^3$ kPa-G (250 psig), at the reaction temperature of 175° C. The reaction was carried out at a constant pressure to yield a solution having the following composition:

50.3 wt % Methyl Acetate
5.6 wt % Acetic Acid
3.3 wt % Methyl Iodide
18.0 wt % (Catalyst, etc.)
22.8 wt % Methanol Selectivity to the formation of the desired ester product was about 88% at about 65% conversion of methanol. No substantial amounts of by-products such as aldehydes, dimethyl ether, higher boiling carboxylic acids, methane, and/or carbon dioxide were formed. The time required for the reaction was 103 minutes. The product distribution of a high proportion of ester was in accordance with the alcohol/ester mole ratio criteria set forth hereinabove for an alcohol/ester mole ratio greater than 10, and a methanol conversion of less than 90%.

In this example after equilibration of the initially charged feed mixture, the solution contained about 37.0 g (0.05 mole) of methyl acetate, 196.0 g (6.12 moles) of methanol, and only about 0.5 g (0.0083 mole) of acetic acid. After the reaction, the solution contained about 163.0 g (2.20 moles) of methyl acetate and 18.0 g (0.30 mole) of acetic acid which corresponds to a net production of 126.0 g (1.70 moles) of methyl acetate and 17.4 g (0.29 moles) of acetic acid.

EXAMPLE 25

A batch reactor was charged with 0.396 g (0.0015 mole) of a rhodium compound having the formula $RhCl_3.3H_2O$, 51.0 g (0.23 mole) of a promoter consisting of aqueous 57% hydriodic acid, 150.0 g (1.92 moles) of benzene as a solvent, and 100.0 g (1.064 moles) of phenol as feedstock. The reactor was pressurized with carbon monoxide to a total pressure of $3.45 \times 10^3$ Kpa-G (500 psig), corresponding to a carbon monoxide partial pressure of about $2.93 \times 10^3$ kPa-G (425 psig), at the reaction temperature of 195° C. The reaction was carried out at a constant pressure to yield a solution containing the following distribution of products:

37.2 wt % Benzoic Acid
62.8 wt % (Catalyst, etc.)

No substantial amounts of by-products such as aldehydes, ether, higher boiling carboxylic acids, or carbon dioxide were formed.

This example demonstrates the ability of the catalyst system to catalyze the carbonylation of aromatic alcohols.

EXAMPLE 26

A batch reactor was charged with 1.04 (0.0015 mol) of a rhodium compound having the formula $[(C_6H_5)_3P]_2RhCOCl$, 51.0 g (0.23 mole) of a promoter consisting of aqueous 57% hydriodic acid, 150.0 g (1.92 moles) of benzene as a solvent, and 82.0 g (0.71 mole) of 1-heptanol as feedstock. The reactor was pressurized with carbon monoxide to a total pressure of $3.45 \times 10^3$ kPa-G (425 psig), at the reaction temperature of 175° C. The reaction was carried out at a constant pressure to yield a solution containing the following distribution of products:

31.1 wt % Octanoic Acid
26.9 wt % (Catalyst, etc.)

No substantial amounts of by-products such as aldehydes, ethers, higher boiling carboxylic acids, paraffins, or carbon dioxide were formed.

This example demonstrates the ability of the catalyst system to catalyze the carbonylation of long chain alcohols.

EXAMPLE 27

A batch reactor was charged with 0.396 g (0.0015 mole) of a rhodium compound having the formula $RhCl_3.3H_2O$, 51.0 g (0.23 mole) of a promoter consisting of aqueous 57% hydriodic acid, 215.0 g (2.91 moles) of tert-buty alcohol as feedstock. The reactor was pressurized with carbon monoxide to a total pressure of $3.45 \times 10^3$ kPa-G (500 psig), corresponding to a carbon monoxide partial pressure of about $2.76 \times 10^3$ kPa-G (400 psig), at the reaction temperature of 195° C. The reaction was carried out at a constant pressure to yield a solution containing the following distribution of products:

82.4 wt % Pivalic Acid
17.6 wt % (Catalyst, etc.)

No substantial amounts of by-products such as aldehydes, ethers, high boiling carboxylic acids, paraffins, or carbon dioxide were formed.

This example demonstrates ability of the catalyst system to catalyze the carbonylation of tertiary alcohols.

EXAMPLE 28

A batch reactor was charged with 0.396 (0.0015 mole) of a rhodium compound having the formula $RhCl_3.3H_2O$, 51.0 g (0.23 mole) of a promoter consisting of aqueous 57% hydriodic acid, 214.0 g (3.57 moles) of isopropyl alcohol as feedstock. The reactor was pressurized with carbon monoxide to a total pressure of $3.45 \times 10^3$ kPa-G (500 psig), corresponding to a carbon monoxide partial pressure of about $2.76 \times 10^3$ kPa-G (400 psig), at the reaction temperature of 175° C. The reaction was carried out at a constant pressure to yield a solution containing the following distribution of products:

79.4 wt % Isobutyric Acid
20.6 wt % (Catalyst, etc.)

No substantial amounts of by-products such as aldehydes, ethers, higher boiling carboxylic acids, paraffins, or carbon dioxide were formed.

This example demonstrates the ability of the catalyst system to catalyze the carbonylation of secondary alcohols.

EXAMPLE 29

A batch reactor was charged with 0.396 g (0.0015 mole) of a rhodium compound having the formula $RhCl_3.3H_2O$, 51.0 g (0.23 mole) of a promoter consisting of aqueous 57 wt % hydriodic acid, 196.9 g (3.28 moles) of acetic acid as a solvent, and 100.0 g (1.11 moles) of 1,4-butanediol as feedstock. The reactor was pressurized with carbon monoxide to a total pressure of $6.893 \times 10^3$ kPa-G (1,000 psig), corresponding to a carbon monoxide partial pressure of about $5.51 \times 10^3$ kPa-G (800 psig), at the reaction temperature of 200° C. The reaction was carried out at constant pressure. The reaction products were subsequently analyzed by gas chromatographic techniques.

The selectivity of the formation of the desired dicarboxylic acid product, adipic acid, which resulted from carbonylation at each alcohol group of the (non-vicinal) diol, was greater than 38 mol %. No substantial amounts of by-products such as aldehydes, higher boiling carboxylic acids, methane, or carbon dioxide were formed.

EXAMPLES 30-47

The procedure of Example 29 was also followed in Examples 30–47, in order to illustrate the variation of parameters. Data of these runs are shown in accompanying Table 2, including variation of catalyst components, feedstock, and reaction conditions along with results for carbonylation product selectivity.

TABLE 2[1]

| Ex. | Carbonylatable Reactant | Catalyst Source Material Rh | Promoter | Solvent | Temp °C. | Reactor Press. kPa-G × $10^3$ | Major Product Selectivity (mol %) |
|---|---|---|---|---|---|---|---|
| 30 | $HO(CH_2)_2OH$[2] | $RhCl_3.3H_2O$ | $HI$[3] | $CH_3COOH$ | 175 | 4.82 | $CH_3CH_2COOH$ (95)[5] |
| 31 | $HO(CH_2)_3OH$ | $RhCl_3.3H_2O$ | $HI$[3] | $CH_3COOH$ | 200 | 6.893 | $HOOC(CH_2)_3COOH$ (30) |
| 32 | $HO(CH_2)_4OH$ | $Rh[P(C_6H_5)_3]_2(CO)Cl$ | $CH_3I$ | $CH_3COOH$ | 175 | 4.82 | $HOOC(CH_2)_4COOH$ (74) |
| 33 | $HO(CH_2)_4OH$ | $Rh[P(C_6H_5)_3]_3Cl$ | $CH_3I$ | $CHCOOH$ | 215 | 7.58 | $HOOC(CH_2)_4COOH$ (22) |
| 34 | $HO(CH_2)_8OH$ | $Rh[P(C_6H_5)_3]_2(CO)Cl$ | $CH_3I$ | $CH_2CH_2COOH$ | 200 | 6.893 | $HOOC(CH_2)_8COOH$ (31) |
| 35 | $HOCH_2CHCH_3$[2] $\|$ $OH$ | $RhCl_3.3H_2O$ | $HI$[4] | $CH_3COOH$ | 200 | 6.893 | $\left[\begin{array}{l}CH_3CH_2CH_2COOH \\ CH_3CHCOOH \\ \quad \| \\ \quad CH_3\end{array}\right]$(95)[5] |
| 36 | $HO(CH_2)_2CHCH_3$ $\|$ $OH$ | $RhI_3$ | $CaI_2.3H_2O$ | $H_2O$ | 200 | 6.893 | $HOOC(CH_2)_2CHCOOH$ (25) $\|$ $CH_3$ |
| 37 | $HOCH_2CH(CH_2)_3CH_3$[2] $\|$ $OH$ | $Rh[P(C_6H_5)_3]_2(CO)Cl$ | $CH_3I$ | $CH_3CH_2COOH$ | 200 | 6.893 | $\left[\begin{array}{l}CH_3(CH_2)_3COOH \\ CH_3(CH_2)_3CHCOOH \\ \quad \| \\ \quad CH_3\end{array}\right]$(65)[5] |
| 38 | $C_6H_5CH_2OH$ | $RhCl_3.3H_2O$ | $HI$[3] | $CH_3COOH$ | 140 | 3.45 | $C_6H_5CH_2COOH$ (90)[5] |
| 39 | $C_6H_5CH_2I$ | $[Rh(CO)_2Br]_2$ | $HI$[5] | $CH_3CH_2COOH$ | 175 | 2.068 | $C_6H_5CH_2COOH$ (83)[5] |
| 40 | $ClCH_2CH_2OH$[2] | $Rh[P(C_6H_5)_3]_3Cl$ | $HI$[3] | $CH_3CH_2COOH$ | 200 | 5.51 | $CH_3CH_2COOH$ (93)[5] |
| 41 | $CH_3-C_6H_4-CH_2OH$ | $Rh_2O_3$ | $HBr$[4] | $CH_3COOH$ | 165 | 4.14 | $CH_3-C_6H_4-CH_2COOH$ (82)[5] |
| 42 | $CH_3O(CH_2)_2OH$[2] | $[Rh(CO)_2Cl]_2$ | $HI$[3] | $CH_3COOH$ | 215 | 7.58 | $CH_3CH_2COOH$ (47)[5] |
| 43 | $CH_2\!-\!\!-\!\!-\!CH\!-\!CH_3$ $\diagdown_{O}\diagup$ | $Rh(NO_3)_3.2H_2O$ | $CaI_2.3H_2O$ | $CH_3COOH$ | 200 | 6.893 | $\left[\begin{array}{l}CH_3CH_2CH_2COOH \\ CH_3CHCOOH \\ \quad \| \\ \quad CH_3\end{array}\right]$(88)[5] |
| 44 | $H_2C\!-\!\!-\!\!-\!CH_2$ $\| \quad\quad \|$ $H_2C\diagdown_{O}\diagup CH_2$ | $RhCl_3.3H_2O$ | $HI$[3] | $CH_3COOH$ | 175 | 4.82 | $\left[\begin{array}{l}HOOC(CH_2)_4COOH\ (14) \\ HOOC(CH_2)_3COOH\ (38)\end{array}\right]$ |
| 45 | $H_2C\!-\!\!-\!\!-\!CH_2$ $\| \quad\quad \|$ $H_2C\diagdown_{O}\diagup CH_2$ | $[Rh(CO)_2Cl]_2$ | $HBr$ | $H_2O$ | 175 | 2.24 | $HOOC(CH_2)_4COOH$ (5) |
| 46 | $m\text{-}C_6H_4(OH)_2$ | $[Rh(CO)_2Br]_2$ | $HBr$[4] | $CH_3CH_2COOH$ | 215 | 7.58 | $m\text{-}C_6H_4(COOH)_2$ (1.4) |
| 47 | $p\text{-}C_6H_4I_2$ | $Rh(NO_3)_3.2H_2O$ | $HI$[3] | $CH_3COOH$ | 200 | 6.893 | $p\text{-}C_6H_4(COOH)_2$ (5) |

[1] Run Conditions: [Rh] × $10^{-3}$ M; [Br or I]0.6 M; 50 ml of solvent; Time: 17 hours
[2] Vicinal or 1,2-disubstituted.
[3] Aqueous, 57 wt %.
[4] Aqueous, 48 wt %.
[5] No dicarboxylic acids detected by gas chromatographic analysis.

EXAMPLE 48

A batch reactor was charged with 0.10 g (0.00038 mole) of a rhodium compound having the formula $RhCl_3.3H_2O$, 6.6 ml (11.2 g, 0.050 mole) of a promoter component consisting of 57 wt % aqueous hydriodic acid (thereby providing a stoichiometric excess of water) 69 ml (72.4 g, 1.21 moles) of glacial acetic acid as solvent, and 14.0 g (0.33 mole) of propylene as feedstock. The reactor was pressurized with carbon monoxide to a total pressure of $4.86 \times 10^3$ kPa-G (705.3 psig), corresponding to a carbon monoxide partial pressure of about $1.97 \times 10^3$ kPa-G (285.3 psig) at the reaction temperature of 175° C. The reaction was carried out at constant pressure to yield a product solution, which upon analysis by gas chromatographic techniques was shown to contain (solvent and catalyst-free bases):

|  | Wt % |
|---|---|
| 2-Iodopropane | 19.0 |
| Isobutyric acid | 50.0 |
| n-Butyric acid | 31.0 |

The selectivity to the desired carboxylic acid product (defined as moles of carboxylic acid/total moles of olefin and/or olefin derivative consumed × 100) was greater than 99 mol % at substantially 80% conversion level. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 49

A glass-lined batch reactor was charged with 0.10 g (0.00038 mole) of a rhodium compound having the formula $RhCl_3 \cdot 3H_2O$, 9 ml (15.3 g, 0.056 mole) of a promoter component consisting of 47 wt % aqueous hydriodic acid, 66 ml (69.2 g, 1.15 moles) of glacial acetic acid as solvent, and 7.0 g (0.25 mole) of ethylene as feedstock. The reactor was pressurized with carbon monoxide to a total pressure of $4.72 \times 10^3$ kPa-G (685.3 psig), corresponding to a carbon monoxide partial pressure of about $1.45 \times 10^3$ kPa-G (210.3 psig) at the reaction temperature of 175° C. The reaction was carried out at constant pressure to yield a product solution, which upon analysis by gas chromatographic techniques was shown to contain (solvent and catalyst-free bases):

|   | Wt % |
|---|---|
| Ethyl iodide | 15.0 |
| Propionic acid | 85.0 |

The selectivity to the desired carboxylic acid product (defined as moles of carboxylic acid/total moles of olefin and/or olefin derivative consumed $\times 100$) was greater than 99 mol % at substantially 85% conversion level. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 50

A batch reactor was charged with 0.133 g (0.00050 mole) of a rhodium compound having the formula $RhCl_3 \cdot 3H_2O$, 8.8 ml (15.0 g, 0.067 mole) of 57 wt % hydriodic acid, 66 ml (69.2 g, 1.15 moles) of glacial acetic acid as solvent, and 16.8 g (0.20 mole) of 1-hexane as feedstock. The reactor was pressurized with carbon monoxide to a total pressure of $4.72 \times 10^3$ kPa-G (685.3 psig), corresponding to a carbon monoxide partial pressure of about $4.034 \times 10^3$ kPa-G (585.3 psig) at the reaction temperature of 175° C. The reaction was carried out at constant pressure. The resultant reaction mixture was analyzed by gas chromatographic techniques and found to contain (solvent and catalyst-free bases):

|   | Wt % |
|---|---|
| Hexenes | 15.0 |
| 2-Iodohexane | 5.0 |
| Branched $C_7$ carboxylic acids | 58.0 |
| Heptanoic acid | 22.0 |

The selectivity to the desired carboxylic acid product (defined as moles of carboxylic acid/total moles of olefin and/or olefin derivative consumed $\times 100$) was greater than 99 mol % at substantially 80% conversion level. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

When the above experiment was repeated except that no HI was employed, no reaction occurred.

EXAMPLE 51

A stirred batch reactor was charged with 0.133 g (0.00050 mole) of a rhodium compound having the formula $RhCl_3 \cdot 3H_2O$, 8.8 ml (15.0 g, 0.067 mole) of a promoter component consisting of 57 wt % aqueous hydriodic acid, 66 ml (69.2 g, 1.15 moles) of glacial acetic acid as solvent, and 16.7 g (0.20 mole) of 2-hexane as feedstock. The reactor was pressurized with carbon monoxide to a total pressure of $4.72 \times 10^3$ kPa-G (685.3 psig), corresponding to a carbon monoxide partial pressure of about $4.034 \times 10^3$ kPa-G (585.3 psig) at the reaction temperature of 175° C. The reaction was carried out at constant pressure. The resultant reaction mixture was analyzed by gas chromatographic techniques and found to contain (solvent and catalyst-free bases):

|   | Wt % |
|---|---|
| Hexenes | 37.0 |
| Miscellaneous intermediates | 34.0 |
| Branched $C_7$ carboxylic acids | 23.0 |
| Heptanoic acid | 6.0 |

The selectivity to the desired carboxylic acid product (defind as moles of carboxylic acid/total moles of olefin and/or olefin derivative consumed $\times 100$) was greater than 99 mol % at substantially 28% conversion level. No substantial amounts of other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 52

A batch reactor was charged with the quantities of ingredients described in Example 51 above except that 20.0 g (0.18 mole) of 1-octene was employed as the feedstock. This mixture provided a water content in 150 mol % excess relative to olefin reacted. The reactor was pressurized with carbon monoxide to a total pressure of $6.79 \times 10^3$ kPa-G (985.3 psig), corresponding to a carbon monoxide partial pressure of about $3.69 \times 10^3$ kPa-G (535.3 psig) at the reaction temperature of 200° C. The reaction was carried out at constant pressure. The resultant reaction mixture was analyzed by gas chromatographic analysis and found to contain (solvent and catalyst-free bases):

|   | Wt % |
|---|---|
| Octenes | 30.0 |
| Iodooctane | Trace |
| Nonanoic acid | 30.0 |
| Branched $C_7$ carboxylic acids | 40.0 |

The selectivity to the desired carboxylic acid product (defined as moles of carboxylic acid/total moles of olefin and/or olefin derivative consumed $\times 100$) was greater than 99 mol % at substantially 70% conversion level. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 53

A batch reactor was charged with 0.10 g (0.00038 mole) of a rhodium compound having the formula RhCl$_3$.3H$_2$O, 17.4 g (0.059 mole) of a promoter component consisting of calcium iodide, 6 ml (6.0 g, 0.33 mole) of water and 69 ml (72.4 g, 1.21 moles) of glacial acetic acid as solvent, and 16.8 g (0.20 mole) of 1-hexane as feedstock. The reactor was presurized with carbon monoxide to a total pressure of 4.72×10$^3$ kPa-G (685.3 psig), corresponding to a carbon monoxide partial pressure of about 4.034×10$^3$ kPa-G (585.3 psig) at the reaction temperature of 175° C. The reaction was carried out at a constant pressure. The reaction mixture was subsequently analyzed by gas chromatographic techniques and found to contain (solvent and catalyst-free bases):

|  | Wt % |
|---|---|
| Hexenes | 16.0 |
| Iodohexane | 6.0 |
| Branched C$_7$ carboxylic acids | 55.0 |
| Heptanoic acid | 23.0 |

The selectivity to the desired carboxylic acid product (defined as moles of carboxylic acid/total moles of olefin and/or olefin derivative consumed×100) was greater than 98 mol % at substantially 83% conversion level. No other organic oxygenated compounds such as alcohols, aldehydes, ketones, etc., were produced as determined by gas chromtographic analysis. No substantial amounts of other undesirable by-products such as methane, carbon dioxide, or higher carboxylic acids were formed.

EXAMPLE 54

A batch reactor was charged with 0.133 g (0.00050 mole) of a rhodium compound having the formula RhCl$_3$.3H$_2$O, 18.3 g (0.067 mole) of a promoter component consisting of 47 wt % aqueous hydriodic acid, 37.8 ml (39.7 g, 0.66 mole) of glacial acetic acid as solvent, and 40.2 g (0.49 mole) of cyclohexane as feedstock. The reactor was pressurized with carbon monoxide to a total pressure of 4.72×10$^3$ kPa-G (685.3 psig), corresponding to a carbon monoxide partial pressure of about 3.86×10$^3$ kPa-G (560.3 psig) at the reaction temperature of 175° C. The reaction was carried out at constant pressure. The reaction mixture was subsequently analyzed by gas chromatographic techniques and found to contain (solvent and catalyst-free bases):

|  | Wt % |
|---|---|
| Cyclohexene | 2.0 |
| Cyclohexane carboxylic acid | 98.0 |

The selectivity to the desired carboxylic acid product (defined as moles of carboxylic acid/total moles of olefin and/or olefin derivative consumed×100) was virtually quantitative. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 55

A batch reactor was charged with 0.10 g (0.00038 mole) of a rhodium compound having the formula RhCl$_3$.3H$_2$O, 13.7 g (0.050 mole) of a promoter component consisting of 47 wt % aqueous hydriodic acid, 65.9 ml (69.1 g, 1.15 moles) of glacial acetic acid as solvent, and 13.0 g (0.24 mole) of 1,3-butadiene as feedstock. The reactor was pressurized with carbon monoxide to a total pressure of 4.72×10$^3$ kPa-G (685.3 psig), corresponding to a carbon monoxide partial pressure of about 3.52×10$^3$ kPa-G (510.3 psig) at the reaction temperature of 175° C. The reaction was carried out at constant pressure. On mole of carbon monoxide was consumed per mole of butadiene charged. The reaction mixture was subsequently analyzed by gas chromatographic techniques and found to contain (solvent and catalyst-free bases) greater than 79 wt % C$_5$ carboxylic acids.

EXAMPLE 56

A batch reactor was charged with 0.097 g (0.000021 mole) of a rhodium compound having the formula Rh$_2$(CO)$_4$Cl$_4$, 9.5 g (0.067 mole) of a promoter component consisting of methyl iodide, 5 ml (5.0 g, 0.28 mole) of distilled water and 45.8 ml (48.1 g, 0.80 mole) of glacial acetic acid as solvent, and 38.6 g (0.24 mole) of 1-dodecene as feedstock. The reactor was pressurized with carbon monoxide to a total pressure of 4.72×10$^3$ kPa-G (685.3 psig), corresponding to a carbon monoxide partial pressure of about 4.21×10$^3$ kPa-G (610.3 psig) at the reaction temperature of 175° C. The reaction was carried out at a constant pressure. The reaction mixture was subsequently analyzed by gas chromatographic techniques and found to contain (solvent and catalyst-free bases):

|  | Wt % |
|---|---|
| Unreacted olefin feedstock | 9.0 |
| Miscellaneous intermediates | 11.0 |
| C$_{13}$ carboxylic acids | 80.0 |

The selectivity to the desired carboxylic acid procut (defined as moles of carboxylic acid/total moles of olefin and/or olefin derivative consumed×100) was greater than 99 mol % at substantially 80% of conversion level. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids are formed.

EXAMPLE 57

A batch reactor was charged with 0.10 g (0.00038 mole) of a rhodium compound having the formula RhCl$_3$.3H$_2$O, 13.7 g (0.050 mole) of a promoter component consisting of 47 wt % aqueous hydriodic acid, 40.9 ml (42.9 g, 0.72 mole) of glacial acetic acid as solvent, and 25.0 g (040 mole) of vinyl chloride as feedstock. The reactor was pressurized with carbon monoxide to a total pressure of 4.72×10$^3$ kPa-G (685.3 psig), corresponding to a carbon monoxide partial pressure of about 3.59×10$^3$ kPa-G (520.3 psig) at the reaction temperature of 175° C. The reaction was carried out at constant pressure. The reaction mixture was subsequently analyzed by gas chromatographic techniques and found to contain (solvent and catalyst-free bases) greater than 34 wt % propionic acid.

EXAMPLE 58

A batch reactor was charged with 0.097 g (0.000021 mole) of formula compound having the formula [Rh(CO)$_2$Cl]$_2$, 14.2 g (0.067 mole) of a promoter component consisting of iodohexane, 61.3 ml (64.3 g, 1.072 moles) of glacial acetic acid as solvent, and 19.3 g (0.23 mole) of 1-hexene as feedstock. The reactor was pressurized with carbon monoxide to a total pressure of 4.72×10$^3$ kPa-G (685.3 psig), corresponding to a carbon monoxide partial pressure of about 4.10×10$^3$ kPa-G (595.3 psig) at the reaction temperature of 175° C. The reaction was carried out at constant pressure. The reaction mixture was subsequently analyzed by gas chromatographic techniques and found to contain (solvent and catalyst-free bases):

|  | Wt % |
| --- | --- |
| Unreacted hexenes and intermediates | 21.0 |
| Branched C$_7$ carboxylic acids | 53.0 |
| Heptanoic acid | 26.0 |

The selectivity to the desired carboxylic acid product (defined as moles of carboxylic acid/total moles of olefin and/or olefin derivative consumed×100) was greater than 99 mol % at substantially 80% conversion level. No other organic oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 59

A batch reaction was charged with 0.133 g (0.00050 mole) of a rhodium compound having the formula RhCl$_3$.3H$_2$O, 15.0 g (0.067 mole) of a promoter component consisting of 57 wt % hydriodic acid, 66.2 ml (69.5 g, 1.16 moles) of glacial acetic acid as solvent, and 29.0 g (0.50 mole) of allyl alcohol as feedstock. The reaction was run under the conditions described in Example 56 above. Gas chromatographic analysis showed the resultant reaction mixture to contain (solvent and catalyst-free bases):

|  | Wt % |
| --- | --- |
| Unreacted intermediates | 9.0 |
| n-Butyric acid | 51.0 |
| Isobutyric acid | 40.0 |

The selectivity to the desired carboxylic acid product (defined as moles of carboxylic acid/total moles of olefin and/or olefin derivative consumed×100) was greater than 90 mol % at substantially 100% conversion level. No other orgainc oxygenated compounds such as alcohols, aldehydes, ketones, etc., were produced as determined by gas chromatographic analysis. No substantial amounts of other undesirable by-products such as methane, carbon dioxide, or higher carboxylic acids were formed.

EXAMPLE 60

This example illustrates the preparation and use of a solid supported catalyst system.

Rhodium trichloride trihydrate (0.30 g, 0.0011 mole) having the formula RhCl$_3$.3H$_2$O, was dissolved in 115 ml of ethanol. The solution was warmed to 60° C., and carbon monoxide was bubbled through the solution until a pale yellow color was obtained, indicating the presence of the monovalent rhodium complex. The solution was cooled and 20 ml (34.0 g, 0.27 mole) of 57 wt % hydriodic acid was added thereto. The resulting solution was added to 20 ml of activated carbon (Pittsburgh Activated Carbon Co.). The excess solvent was evaporated using a rotary evaporator under vacuum. The resultant catalyst was vacuum dried at 60° C. for about 16 hours. The catalyst was then preheated in nitrogen at 200° C. for one hour.

The above prepared solid supported catalyst (10 ml) was charged to a 45.72-cm (18-inch) Pyrex glass vertical reactor 30 mm (1.18 inches) in diameter. The resulting catalyst bed, 2 cm in depth, was covered with 100 ml of inert packing as a preheater. Gaseous ethylene was supplied to the reactor and was subsequently converted to propionic acid at high selectivity. The reaction was conducted at a feed rate (moles/hour) of ethylene, 0.27; HI, 0.02; water, 0.28; and CO, 0.54. This feed mixture provided the water in a 3.7 mol % excess relative to the ethylene. The pressure at which the gaseous reactants contacted the solid supported catalyst was 3.35×10$^3$ kPa-G (485.3 psig), corresponding to a carbon monoxide partial pressure of about 7.60×10$^2$ kPa-G (110.3 psig) at a reaction temperature of 175° C.

The gaseous reactor effluent contained, as determined by gas chromatographic analysis, propionic acid, unreacted ethylene, water, carbon monoxide, iodide-containing promoter component. The selectivity of ethylene conversion to propionic acid was virtually quantitative.

EXAMPLE 61

A batch reactor was charged with 0.133 g (0.00050 mole) of a rhodium compound having the formula RhCl$_3$.3H$_2$O, 13.6 g (0.050 mole) of a promoter component consisting of 47 wt % aqueous hydriodic acid, 34.8 ml (36.5 g, 0.61 mole) of glacial acetic acid as solvent, and 45.0 g (0.42 mole) of 1,5-cyclooctadiene. The reactor was pressurized with carbon monoxide to a total pressure of 4.72×10$^3$ kPa-G (685.3 psig), corresponding to 4.38×10$^3$ kPa-G (635.3 psig) at the reaction temperature of 175° C. The reaction was carried out at constant pressure. Upon analysis by gas chromatography, the reaction mixture was found to contain (solvent and catalyst-free bases) 77 wt % cyclooctane carboxylic acid.

EXAMPLE 62

A batch reactor was charged with 0.133 g (0.00050 mole) of a rhodium compound having the formula RhCl$_3$.3H$_2$O, 18.3 g (0.067 mole) of a promoter component consisting of 47 wt % aqueous hydriodic acid, 38 ml (39.9 g, 0.66 mole) of glacial acetic acid as solvent, and 40.0 g (0.25 mole) of 1,5,9-cyclododecatriene as feedstock. The reactor was pressurized with carbon monoxide to a total pressure of 3.35×10$^3$ kPa-G (485.3 psig), corresponding to a carbon monoxide partial pressure of about 2.76×10$^3$ kPa-G (400.3 psig) at the reaction temperature of 140° C. The reaction was carried out at constant pressure. Upon analysis by gas chromatography, the reaction mixture was found to contain (solvent and catalyst-free bases):

|  | Wt % |
| --- | --- |
| Unreacted olefin feedstock | 6.0 |
| Intermediates and others | 12.0 |
| Cyclododecane carboxylic acid | 82.0 |

The selectivity to the desired carboxylic acid product was greater than 95 mol % at substantially 85% conversion level.

EXAMPLE 63

A batch reactor was charged with 0.35 g (0.00051 mole) of a rhodium compound having the formula $Rh(CO)Cl[P(C_6H_5)_3]_2$, 12 ml (12.0 g, 0.67 mole) of water, 8.5 g (0.033 mole) of a promoter component consisting of elemental iodine, 38 ml (39.9 g, 0.66 mole) of acetic acid as solvent, and 33.0 g (0.39 mole) of 1-hexene as feedstock. The reactor was pressurized with carbon monoxide to a total pressure of $4.72 \times 10^3$ kPa-G (685.3 psig), corresponding to a carbon monoxide partial pressure of about $4.034 \times 10^3$ kPa-G (585.3 psig) at the reaction temperature of 175° C. The reaction was carried out at constant pressure. The resultant reaction mixture was subsequently analyzed by gas chromatographic techniques and found to contain (solvent and catalyst-free bases) substantially the same product distribution as in Example 53 above.

Examples 64–78 were carried out under substantially anhydrous conditions to produce carboxylic acid anhydrides.

EXAMPLE 64

A batch autoclave was charged with 69.0 g (0.93 mole) of methyl acetate, 20.0 g (0.33 mole) of acetic acid, 0.2 g (0.00076 mole) of rhodium chloride trihydrate, 2.65 g (0.010 mole) of triphenylphosphine, 14.2 g (0.10 mole) of methyl iodide, and 0.8 g (0.012 mole) of lithium acetate. The autoclave was pressured to $2.068 \times 10^3$ kPa-G (300 psig) with a gas mixture of 96% by volume carbon monoxide and 4% by volume hydrogen. The autoclave was heated to 175° C. with stirring and maintained at 175° C. and $3.45 \times 10^3$ kPa-G (500 psig) pressure for a total of 6 hours reaction time. The reaction product was analyzed by gas chromatography and found to contain 64.8 wt % of acetic anhydride.

EXAMPLE 65 (COMPARATIVE)

The procedure of Example 64 above was repeated except that the rhodium chloride trihydrate was replaced by an equivalent amount of anhydrous cobalt chloride. After a total of 6 hours reaction time, the reaction product was analyzed by gas chromatography and found to contain no detectable amount of acetic anhydride.

EXAMPLE 66 (COMPARATIVE)

The purpose of this experiment was to confirm the results obtained in Reppe et al, U.S. Pat. No. 2,730,546.

The procedure described in Example 1 of Reppe et al, was repeated substantially as follows: A rotating autoclave was charged with 50.0 g (0.68 mole) of methyl acetate, 50.0 g (0.50 mole) of N-methylpyrrolidone, and 10.0 g of a catalyst consisting of 2.0 g (0.0067 mole) of anhydrous cobalt bromide, 3.0 g (0.012 mole) of tetraethylammonium iodide and 5.0 (0.013 mole) of triphenylbutylphosphonium bromide. A mixture of 90.9 volume % (10 parts by volume) of carbon monoxide and 9.1 volume % (1 part by volume) of hydrogen was then added to the autoclave at 180° C. under a pressure of $2.068 \times 10^4$ kPa-G (3,000 psig) and for a total reaction time of 17 hours and 40 minutes. The reaction product was analyzed by gas chromatography and a total of 20.9 wt % (parts) of acetic anhydride was obtained.

This experiment varied slightly from the procedure described in Example 1 of U.S. Pat. No. 2,730,546 with resepct to the pressure and total reaction time. In that Example, the pressure was 200 atmospheres which is equivalent to exactly $2.027 \times 10^4$ kPa-G (2,940 psig). The variance in pressure of $4.14 \times 10^2$ kPa-G (60 psig) is only about 2% and this slightly higher pressure would not substantially affect the results of the reaction. In fact, if such higher pressure did have any effect it would be beneficial since Reppe et al discloses that pressures between 200 and 300 atmospheres ($2.027 \times 10^4$ kPa-G and $3.040 \times 10^4$ kPa-G) are most preferred (Reppe et al, column 2, lines 51–52). A longer total reaction time, 17 hours and 40 minutes versus the 15 hours total reaction time in Reppe et al, was employed to ensure that the reaction was complete. The higher amount of acetic anhydride obtained, 20.9 wt % (parts) versus 18.0 wt % (parts), merely confirms that more product is obtained at longer reaction time.

EXAMPLE 67

A batch autoclave reactor was charged with 0.308 g (0.0010 mole) $Rh_2O_3 \cdot 3H_2O$, 28.4 g (0.20 mole) methyl iodide, 14.5 g (0.315 mole) dimethyl ether, and sufficient acetic acid to produce a total volume of 100 ml. The reactor was then supplied with carbon monoxide at a constant pressure for the reaction periods indicated below and maintained at 175° C. during the entire reaction period. Three different constant pressures were maintained during the series of runs. At the end of the reaction period, the reactor was cooled and vented. The resultant liquid was analyzed by gas chromatography. The following table sets forth the results obtained in the series of runs wherein the reaction pressure was varied.

| Pressure kPa-G × 10³ | Run Time (Hrs) | Carbonylation Product, wt % (methyl iodide and acetic acid-free bases) | | |
| --- | --- | --- | --- | --- |
|  |  | Dimethyl Ether | Methyl Acetate | Acetic Anhydride |
| 3.45 | 19.5 | 0.5 | 32.0 | 67.5 |
| 4.14 | 18.8 | 0.5 | 26.9 | 72.6 |
| 4.83 | 23.6 | 0.4 | 22.6 | 77.0 |

EXAMPLE 68

A batch autoclave reactor was charged with 0.77 g (0.0025 mole) $Rh_2O_3 \cdot 3H_2O$, 28.4 g (0.20 mole) methyl iodide, 14.5 g (0.315 mole) dimethyl ether, and sufficient acetic acid to produce a total volume of 100 ml. The reactor was then supplied with carbon monoxide at a constant pressure of $3.45 \times 10^3$ kPa-G (500 psig) for the reaction periods as indicated below. During the series of runs, four different reaction temperatures were utilized. At the end of the indicated reaction periods, the reactor was cooled and vented. The resultant liquid was analyzed by gas chromatography. The results of the four runs, at differing reaction temperatures are set forth in the table below:

| Temp. (°C.) | Run Time (Hrs) | Carbonylation Product, wt % (methyl iodide and acetic acid-free bases) | | |
|---|---|---|---|---|
| | | Dimethyl Ether | Methyl Acetate | Acetic Anhydride |
| 125 | 17.1 | 0.0 | 20.7 | 79.3 |
| 150 | 18.0 | 0.0 | 25.0 | 75.0 |
| 175 | 18.0 | 0.8 | 30.2 | 69.0 |
| 190 | 18.0 | 0.7 | 40.8 | 58.5 |

EXAMPLE 69

A series of runs was carried out to show the effects of rhodium compound concentration on the production of acetic anhydride from dimethyl ether. In this series of runs, a batch autoclave reactor was charged with varying amounts of $Rh_2O_3.3H_2O$. In all three runs, 28.4 g (0.20 mole) of methyl iodide, 14.5 g (0.315) dimethyl ether, and sufficient acetic acid solvent to produce a total volume of 100 ml were charged to the reactor. The reactor was then supplied with carbon monoxide at a constant pressure of $3.45 \times 10^3$ kPa-G (500 psig) and was maintained at 175° C. for the time indicated in the table below. The following table shows the results of this series of runs with the wt % analysis of the product determined by gas chromatography analysis.

| $Rh_2O_3.3H_2O$ (g, mole) | Run Time (Hrs) | Carbonylation Product, wt % (methyl iodide and acetic acid-free bases) | |
|---|---|---|---|
| | | Methyl Acetate | Acetic Anhydride |
| 0.154, 0.0005 | 30.5 | 36.0 | 64.0 |
| 0.308, 0.001 | 24.0 | 32.0 | 68.0 |
| 100.396, 0.0015 | 24.0 | 31.0 | 69.0 |

EXAMPLE 70

A batch autoclave reactor was charged with 0.308 g (0.0010 mole) $Rh_2O_3.3H_2O$, 14.2 g (0.10 mole) methyl iodide, and varying amounts of methyl acetate as set forth below and sufficient acetic acid to produce a total volume of 100 ml. The reactor was supplied with carbon monoxide at a constant pressure of $3.45 \times 10^3$ kPa-G (500 psig) and maintained at 175° C. for the indicated reaction period. At the end of the reaction period, the reactor was cooled and vented. The liquid was analyzed by gas chromatography. The results observed from the series of runs using differing amounts of methyl acetate are set forth in the table below:

| Methyl Acetate (g, mole) | Run Time (Hrs) | Carbonylation Product, wt % (methyl iodide and acetic acid-free bases) | |
|---|---|---|---|
| | | Methyl Acetate | Acetic Anhydride |
| 9.9, 0.160 | 18.3 | 18.8 | 81.2 |
| 19.5, 0.315 | 19.2 | 19.1 | 80.9 |
| 39.06, 0.630 | 22.0 | 33.7 | 66.3 |

EXAMPLE 71

A batch autoclave reactor was charged with 0.2 g (0.0010 mole) of $RhCl_3$, 29.4 g (0.10 mole) of calcium iodide, 31.0 g (0.50 mole) of methyl acetate, 2.6 g (0.010 mole) of triphenylphosphine, and 71.4 g (1.19 moles) of acetic acid. The reactor was supplied with carbon monoxide at a constant pressure of $3.45 \times 10^3$ kPa-G (500 psig) for 100 minutes at 205° C. At the end of the reaction period, the reactor was cooled and vented. The resultant liquid was analyzed by gas chromatography. The wt % analysis of the liquid product was 22.06% acetic anhydride, 15.52% methyl iodide, 5.98% methyl acetate, and 56.01% acetic acid.

EXAMPLE 72

A batch autoclave reactor was charged with 0.2 g (0.0010 mole) of $RhCl_3$, 26.8 g (0.20 mole) of lithium iodide, 31.0 g (0.50 mole) of methyl acetate, 2.6 g (0.010 mole) of triphenylphosphine, and 66.6 g (1.11 moles) of acetic acid. The reactor was supplied with carbon monoxide at a constant pressure of $3.45 \times 10^3$ kPa-G (500 psig) for 2.1 hours at 205° C. At the end of the reaction period, the reactor was cooled and vented. The resultant liquid was analyzed by gas chromatography. The wt % analysis of the liquid product was 23.5% acetic anhydride, 7.1% methyl iodide, 4.7% methyl acetate, and 64.3% acetic acid.

EXAMPLE 73

A batch autoclave reactor was charged with 0.003 g (0.0010 mole) of $RhCl_3$, 14.2 g (0.10 mole) of methyl iodide, and 72.8 g (1,175 moles) of methyl acetate. The reactor was supplied with carbon monoxide at a constant pressure of $3.45 \times 10^3$ kPa-G (500 psig) for 6 hours at 175° C. At the end of the reaction period the reactor was cooled and vented. The liquid was analyzed by gas chromatography. The wt % analysis of the liquid product was 2.67% acetic anhydride, 9.5% methyl iodide, 84.7% methyl acetate, and 2.6% acetic acid.

EXAMPLE 74

A batch autoclave reactor was charged with 0.2 g (0.0010 mole) of $RhCl_3$, 30.0 g (0.20 mole) of sodium idodide, 31.0 g (0.50 mole) of methyl acetate, 66.6 g (1.11 moles) of acetic acid, and 2.6 g (0.010 mole) of triphenylphosphine. The reactor was supplied with carbon monoxide at a constant pressure of $3.45 \times 10^3$ kPa-G (500 psig) for 2.4 hours at 205° C. At the end of the reaction period the reactor was cooled and vented. The resultant liquid was analyzed by gas chromatography. The wt % analysis of the liquid product was 26.7% acetic anhydride, 1.7% methyl iodide, 5.7% methyl acetate, and 65.6% acetic acid.

EXAMPLE 75

A batch autoclave reactor was charged with 0.2 g (0.0010 mole) of $RhCl_3$, 33.2 (0.20 mole) of potassium iodide, 2.6 (0.010 mole) of triphenylphosphine, 31.0 g (0.50 mole) of methyl acetate, and 66.6 g (1.11 moles) of acetic acid. The reactor was supplied with carbon monoxide at a constant pressure of $3.45 \times 10^3$ kPa-G (500 psig) for 4.25 hours at 205° C. At the end of the reaction period, the reactor was cooled and vented. The resultant liquid was analyzed by gas chromatography. The wt % of analysis of the liquid product was 29.2% acetic anhydride, 0.5% methyl iodide, 10.6% methyl acetate, and 59.2% acetic acid.

EXAMPLE 76

To produce glutaric anhydride, a batch autoclave reactor was charged with 0.2 g (0.0010 mole) of $RhCl_3$, 13.4 g (0.10 mole) of lithium iodide, 34.4 g (0.40 mole) of γ-butyrolacetone, 51.6 g (0.86 mole) of acetic acid, and 2.6 g (0.010 mole) of triphenylphoshine. The reactor was supplied with carbon monoxide at a constant pressure of $3.45 \times 10^3$ kPa-G (500 psig) for 23 hours at 205° C.

EXAMPLE 77

To produce phenylacetic anhydride, a batch autoclave reactor was charged with 0.2 g (0.0010 mole) of $RhCl_3$, 13.4 g (0.10 mole) of lithium iodide, 39.6 g (0.20 mole) of dibenzyl ether, 51.6 g (0.86 mole) of acetic acid, and 2.6 g (0.010 mole) of triphenylphosphine. The reactor was supplied with carbon monoxide at a constant pressure of $3.45 \times 10^3$ kPa-G (500 psig) for 4.5 hours at 205° C. At the end of the reaction period, the reactor was cooled and vented. The resultant liquid was analyzed by gas chromatography and found to contain phenylacetic anhydride.

EXAMPLE 78

A batch autoclave reactor was charged with 0.258 g (0.00098 mole) of $RhCl_3 \cdot 3H_2O$, 4.85 g (0.038 mole) of hydrogen iodide, 1.53 g (0.015 mole) of acetic anhydride, 76.5 g (1.28 mole) of acetic acid, 3.144 g (0.012 mole) of phenylphoshine, and 30.5 (0.10 mole) of pentaerythrityl tetraacetate. Carbon monoxide at a constant pressure of $3.45 \times 10^3$ kPa-G (500 psig) was supplied to the reactor for 21 hours while the reactor was maintained at 205° C. Following cooling and venting of the reactor, the reaction product was found to contain a mixture of anhydrides having the following average formula:

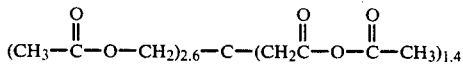

Thus, it is apparent that there has been provided in accordance with the instant invention, a catalyst system that fully satisfies the objects and advantages set forth hereinabove. While the invention has been described with respect to various specific examples and embodiments thereof it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A catalyst system for the production of carbonylation products by the reaction of a carbonylatable reactant and carbon monoxide which consists essentially of:
   (a) a rhodium-containing catalytically active component, the component comprising an adduct of a rhodium-containing component source material and carbon monoxide, and
   (b) a separately added iodine-containing promoter component, the promoter component being selected from the group consisting of iodine and iodide compounds,
   wherein the separately added iodine atoms of (b) are in excess of the rhodium atoms in the catalyst.

2. The catalyst system of claim 1 wherein the rhodium-containing component source material is a rhodium coordination compound.

3. The catalyst system of claim 2 wherein the rhodium coordination compound is rhodium dicarbonyl iodide.

4. The catalyst system of claim 2 wherein the rhodium coordination compound is rhodium bis(triphenylphosphino)carbonyl chloride.

5. The catalyst system of claim 1 wherein the iodide compound is hydrogen iodide.

6. The catalyst system of claim 1 wherein the iodide compound is an alkyl iodide.

7. The catalyst system of claim 6 wherein the alkyl iodide is methyl iodide.

8. The catalyst system of claim 1 wherein the catalyst system is in solution form.

9. The catalyst system of claim 8 wherein the concentration of the rhodium-containing catalytically active component in the solution is between $10^{-6}$ molar and $10^{-1}$ molar.

10. The catalyst system of claim 9 wherein the concentration of the rhodium-containing catalytically active component in the solution is between $10^{-4}$ molar and $10^{-2}$ molar.

11. The catalyst system of claim 1 wherein the rhodium-containing catalytically active component is dispersed upon an inert support.

12. The catalyst system of claim 11 wherein the inert support is selected from the group consisting of activated carbon, clays, alumina, silica and silica-alumina.

13. A catalyst system according to claim 1 wherein the rhodium-containing component source material is a rhodium trihalide and the separately added iodine-containing promoter component is methyl iodide.

* * * * *